(12) United States Patent
Furnas

(10) Patent No.: US 11,035,730 B2
(45) Date of Patent: Jun. 15, 2021

(54) SYSTEMS AND METHODS FOR CHARACTERIZING HIGH-SCATTER GLASS-BASED SAMPLES USING LIGHT-SCATTERING POLARIMETRY

(71) Applicant: CORNING INCORPORATED, Corning, NY (US)

(72) Inventor: William John Furnas, Elmira, NY (US)

(73) Assignee: CORNING INCORPORATED, Corning, NY (US)

( * ) Notice: Subject to any disclaimer, the term of this patent is extended or adjusted under 35 U.S.C. 154(b) by 43 days.

(21) Appl. No.: 16/667,183

(22) Filed: Oct. 29, 2019

(65) Prior Publication Data

US 2020/0132548 A1 Apr. 30, 2020

Related U.S. Application Data

(60) Provisional application No. 62/753,388, filed on Oct. 31, 2018.

(51) Int. Cl.
*G01N 21/00* (2006.01)
*G01J 3/447* (2006.01)
*G01N 21/47* (2006.01)

(52) U.S. Cl.
CPC .............. *G01J 3/447* (2013.01); *G01N 21/47* (2013.01); *G01N 2021/4735* (2013.01); *G01N 2021/4792* (2013.01)

(58) Field of Classification Search
CPC ........... G01M 11/3145; G01M 11/335; G01M 11/33; G01M 11/3109; G01M 11/338

(Continued)

(56) References Cited

U.S. PATENT DOCUMENTS 4,655,589 A 4/1987 Cestaro et al.
5,280,334 A 1/1994 Gisin et al.
(Continued)

FOREIGN PATENT DOCUMENTS

DE 10161914 C1 9/2003
EP 878702 A2 11/1998
(Continued)

OTHER PUBLICATIONS

International Search Report and Written Opinion of the European International Searching Authority; PCT/US2019/057854; dated Jan. 27, 2020; 15 Pgs.

(Continued)

*Primary Examiner* — Md M Rahman
(74) *Attorney, Agent, or Firm* — Kevin M. Johnson

(57) ABSTRACT

Methods of characterizing an optical retardance or a stress-related property of a glass-bases sample include directing a light beam into the glass-based sample while varying the polarization of the light beam to generate scattered light for each polarization are provided. The scattered light for each polarization is captured with an image sensor, which has an exposure time and a frame rate. The scattered light has an intensity distribution at the image sensor. The sample is moved so that the image sensor averages two or more different intensity distributions per frame to form an averaged intensity distribution for each polarization. The averaged intensity distributions for multiple frames are then used to characterize the optical retardance. The optical retardance can turn be used to determine stress-related properties of the glass-based sample. Moving the substrate reduces measurement noise scattered light having no optical retardance information.

20 Claims, 15 Drawing Sheets

(58) Field of Classification Search
USPC .......................................................... 356/327
See application file for complete search history.

(56) References Cited

U.S. PATENT DOCUMENTS

| | | | |
|---|---|---|---|
| 6,370,407 | B1 | 4/2002 | Kroeger et al. |
| 6,924,893 | B2 | 8/2005 | Oldenbourg et al. |
| 7,372,567 | B2 | 5/2008 | Shribak et al. |
| 8,049,871 | B2 | 11/2011 | Furnas et al. |
| 8,094,293 | B2 | 1/2012 | Furnas et al. |
| 8,854,623 | B2 | 10/2014 | Fontaine et al. |
| 2003/0076487 | A1 | 4/2003 | Cannon et al. |
| 2004/0081412 | A1* | 4/2004 | Cocchini ........... C03B 37/01486 385/104 |
| 2008/0237928 | A1* | 10/2008 | Washiya ................. B29C 41/28 264/291 |
| 2010/0027008 | A1 | 2/2010 | Bornhop et al. |
| 2018/0180530 | A1 | 6/2018 | Levitz et al. |

FOREIGN PATENT DOCUMENTS

| | | |
|---|---|---|
| GB | 190101139 A | 11/1901 |
| JP | 2015175830 A | 10/2015 |

OTHER PUBLICATIONS

Aben et al; "On Non-Destructive Residual Stress Measurement in Glass Panels"; Estonian Journal of Engineering, 16, 2 (2010) pp. 150-156.

Anton et al; "A Compact Scattered Light Polariscope for Residual Stress Measurement in Glass Plates," Institute of Cybernetics. A Poster Presented at the Glass Processing Days Show in Tempere, Finland, on Jun. 15-18, 2003; 3 Pages.

Brodland et al; "Curved-Ray Technique to Measure the Stress Profile in Tempered Glass"; Opt. Eng. 39 (9) pp. 2501-2505 (2000).

Glasstress; "Glass Stress Measurement Equipment"; (2019) 1 Page; https://www.glasstress.com/web/.

Opto Engineering; TC4K Series, Flat Telecentric Lenses for 4 K Pixel Linescan Cameras; 2 Pages; Downloaded Jan. 10, 2020 https://www.opto-e.com/products/TC4K-flat-telecentric-optics-for-linescan-4K-detectors.

Scheimpflug Principle; Wikipedia; 9 Pages; (2019).

* cited by examiner

SYSTEMS AND METHODS FOR CHARACTERIZING HIGH-SCATTER GLASS-BASED SAMPLES USING LIGHT-SCATTERING POLARIMETRY

CROSS-REFERENCE TO RELATED APPLICATIONS

This application claims the benefit of priority of U.S. Provisional Application Ser. No. 62/753,388 on Oct. 31, 2018, the content of which is relied upon and incorporated herein by reference in its entirety.

FIELD

The present disclosure relates to characterizing glass-based samples, and in particular to systems and methods for characterizing high-scatter glass-based samples using light-scattering polarimetry.

BACKGROUND

Light-scattering polarimetry uses scattered polarized light to determine stress-based characteristics of items ("samples") capable of scattering light from within the sample material. The sample is irradiated with input laser light at a relatively shallow angle through a coupling prism. The laser light polarization is varied continuously between different polarization states using an optical compensator. The scattered light is detected by an image sensor. Stress in the sample causes optical retardation along the light path, with the amount of stress being proportional to the derivative of the optical retardation. The amount of optical retardation can be determined from the detected scattered light intensity distribution, which varies due to the constructive and destructive interference for the different effective path lengths of the detected light. The stress-related properties that can be measured include stress profiles, central tension (CT) and depth of compression (DOC).

Light-scattering polarimetry works well when the scattered light is generated mainly if not entirely by Rayleigh scattering in the sample providing a stress-based polarization retardation signal. However, light can also be scattered by other mechanisms within a sample, such by scattering centers, micro-particles, inhomogeneities, crystal structure, Mie or non-selective scattering, multiple scattering, etc. Such light scattering represents noise that is not stress based and can obfuscate the stress characterization.

SUMMARY

Aspects of the disclosure are directed to methods of characterizing an optical retardance and one or more stress-related properties of a glass-based sample. The methods include directing a light beam into the glass-based sample while varying the polarization of the light beam. This generates scattered light for each polarization. The scattered light for each polarization is captured with an image sensor, which has an exposure time and a frame rate. The scattered light has an intensity distribution at the image sensor. The sample is moved during the measurement so that the image sensor averages two or more different intensity distributions to form an averaged intensity distribution for each polarization. The averaging can be an integration over the pixel response time within a given frame or it can be a direct averaging of two or more captured intensity distributions. The averaged intensities associated with multiple frames are then used to characterize the optical retardance. The optical retardance can then be used to determine stress-related properties of the glass-based sample. Moving the substrate reduces measurement noise from scattered light having stress profile related no optical retardance information.

A first embodiment (1) of the disclosure is directed to a method of using light-scattering polarimetry to characterize an optical retardance of a glass-based sample. The first method comprises: a) directing a light beam from a light source into the glass-based sample while varying a polarization of the light beam between at least first and second polarization states to generate scattered light for each polarization state; b) for each of the at least first and second polarization states, capturing the scattered light with an image sensor having an exposure time $t_E$ and that captures frames at a frame rate FR, wherein the scattered light has an intensity distribution at the image sensor; c) moving the sample at a sample speed SS relative to at least one of the light beam and the image sensor so that for each of the at least first and second polarization states, the image sensor averages two or more of the intensity distributions per frame to form an averaged intensity distribution; and d) using the averaged intensity distribution for each of at least first and second polarization states to characterize the optical retardance.

A second embodiment (2) of the disclosure is based on embodiment (1) as described above, and further comprising using the characterized optical retardance of act d) to determine at least one stress-related characteristic of the glass-based sample.

A third embodiment (3) of the disclosure is based on any of embodiments (1) and (2), wherein the at least one stress-related characteristic is selected from the group of stress-related characteristics comprising: a stress profile, a surface stress, a depth of compression, a center tension, and a birefringence profile.

A fourth embodiment (4) of the disclosure is based on any of the embodiments (1) through (3), wherein the glass-based sample consists entirely of either a glass material or a glass ceramic material.

A fifth embodiment (5) of the disclosure is based on any of the embodiments (1) through (4), wherein the act c) of moving the glass-based sample at a sample speed SS relative to at least one of the light beam and image sensor comprises moving the glass-based sample while keeping the light beam and image sensor stationary.

A sixth embodiment (6) of the disclosure is based on any of the embodiments (1) through (5), wherein the act c) comprises moving the glass-based sample at the sample speed SS of at least 0.4 millimeters per second.

A seventh embodiment (7) of the disclosure is based on any of the embodiments (1) through (6), wherein the act c) comprises moving the glass-based sample at the sample speed $SS \geq K \cdot \lambda / t_E$, where $\lambda$ is a wavelength of the light beam and K is in the range from 0.4 to 1.

An eighth embodiment (8) of the disclosure is based on any of the embodiments (1) through (7), wherein the light beam resides in an incident plane and further comprising moving the glass-based sample in a direction perpendicular to the incident plane.

A ninth embodiment (9) of the disclosure is based on any of the embodiments (1) through (8), wherein the glass-based sample has a side, and wherein the act c) of moving the glass-based sample comprises pushing the glass-based sample from the side.

A tenth embodiment (10) of the disclosure is based on any of the embodiments (1) through (9), wherein the glass-based sample has a side having a side portion, and wherein the act c) of moving the glass-based sample comprises: operably engaging at least one of the side and the side portion with an engagement fixture; and moving the engagement fixture.

An eleventh embodiment (11) of the disclosure is based on any of the embodiments (1) through (10), wherein the act of moving the sample includes a translation, a rotation, or a combination thereof.

A twelfth embodiment (12) of the disclosure is based on any of the embodiments (1) through (11), wherein the act c) of moving the glass-based sample comprises: operably supporting the glass-based sample in a frame; operably engaging the frame with an engagement fixture; and moving the engagement fixture.

A thirteenth embodiment (13) of the disclosure is based on any of the embodiments (1) through (12), wherein the act c) of moving the glass-based sample comprises moving one or both of the laser source and the image sensor while keeping the glass-based sample stationary.

A fourteenth embodiment (14) of the disclosure is directed to a method of determining a stress-based characteristic of a glass-based sample using light-scattering polarimetry, comprising: operably arranging the glass-based sample in or relative to a polarimeter having an image sensing device, a light source that emits a light beam, and an optical compensator that defines at least first and second polarizations of the light beam; while moving the glass-based sample relative to the at least one of the light source and the image sensing device, directing the light into the glass based sample to generate scattered light that forms at the image sensing device a line image having a time-varying intensity distribution; for each of the first and second polarizations, detecting with the image sensing device at least two substantially different intensity distributions; forming an averaged intensity distribution from the at least two substantially different intensity distributions calculating an optical retardation using the averaged intensity distributions for the at least first and second polarizations; and determining the at least one stress-based characteristic from the optical retardation.

A fifteenth embodiment (15) of the disclosure is based the embodiment (14), wherein forming the averaged intensity distribution comprises detecting the at least two substantially different intensity distributions within a frame of an image sensor that has a frame rate FR.

A sixteenth embodiment (16) of the disclosure is based on any of the embodiments (14) and (15), wherein each of the at least two substantially different intensity distributions are detected within an exposure time $t_E$ of between 0.05 millisecond and 100 milliseconds and at the frame rate FR of between 10 and 200 frames per second.

A seventeenth embodiment (17) of the disclosure is based on any of the embodiments (14) through (16), wherein the calculating of the optical retardation utilizes between two and two-hundred frames over a measurement time $t_M$ of between 0.1 seconds and 10 seconds.

An eighteenth embodiment (18) of the disclosure is based on any of the embodiments (14) through (17), wherein the glass-based sample consists entirely of either a glass material or a glass ceramic material.

A nineteenth embodiment (19) of the disclosure is based on any of the embodiments (14) through (18), wherein moving the glass-based sample relative to the at least one of the light source and the image sensing device comprises moving the glass-based sample while keeping the light source and image sensing device stationary.

A twentieth embodiment (20) of the disclosure is based on any of the embodiments (14) through (19), wherein the moving of the glass-based sample relative to the at least one of the light source and the image sensing device comprises moving one or both of the laser source and the image sensing device while keeping the glass-based sample stationary.

A twenty-first embodiment (21) of the disclosure is based on any of the embodiments (14) through (20), wherein moving the glass-based sample is performed at a speed of at least 0.75 millimeters per second.

A twenty-second embodiment (22) of the disclosure is based on any of the embodiments (14) through (21), wherein the light beam resides in an incident plane and further comprising moving the glass-based sample in a direction perpendicular to the incident plane.

A twenty-third embodiment (23) of the disclosure is based on any of the embodiments (14) through (22), wherein the glass-based sample has a side having a side portion, and the moving of the glass-based sample comprises: operably engaging at least one of the side and the side portion with an engagement fixture; and moving the engagement fixture.

A twenty-fourth embodiment (24) of the disclosure is based on any of the embodiments (14) through (23), wherein the of moving the glass-based sample comprises: operably supporting the glass-based sample in a frame; operably engaging the frame with an engagement fixture; and moving the engagement fixture.

A twenty-fifth embodiment (25) of the disclosure is directed to a method of measuring at least one stress-based characteristic of a glass-based sample having a body. The method comprising: a) performing a polarimetry measurement of the glass-based sample for at least first and second polarization states of light having a wavelength and transmitted into the body of the sample to generate scattered light; b) during act a), detecting for each of the at least first and second polarization states at least first and second light distributions of the scattered light from different portions of the body and averaging the at least first and second light distributions to form an averaged light distribution; c) using the averaged light distribution for each of the first and second polarization states to calculate an optical retardance as a function of depth into the body of the glass-based sample; and d) using the calculated optical retardance to determine the at least one stress-based characteristic of the glass-based sample.

A twenty-sixth embodiment (26) of the disclosure is based on the embodiment (25), wherein said averaging is performed by detecting the at least first and second light distributions within a single frame of an image sensor.

A twenty-seventh embodiment (27) of the disclosure is based on any of the embodiments (25) and (26), wherein the at least first and second light distributions are formed by taking respective at least first and second exposures each having an exposure time $t_E$.

A twenty-eighth embodiment (28) of the disclosure is based on any of the embodiments (25) through (27), and further comprises during act a), moving the glass-based sample so that the different portions of the body are spaced apart by at least one half the wavelength of the light.

A twenty-ninth embodiment (29) of the disclosure is based on any of the embodiments (25) through (28), wherein the movement of the glass-based sample has a sample speed $SS \geq K \cdot \lambda / t_E$, where $t_E$ is an exposure time for the first and second exposures used to capture the first and second light distributions, and K is in the range from 0.4 to 1.

A thirtieth embodiment (30) of the disclosure is based on any of the embodiments (25) through (29), wherein the glass-based sample has a side and is supported on a support surface, and wherein moving the glass-based sample includes pushing the glass-based sample at the side so that the glass-based sample slides over the support surface.

A thirty-first embodiment (31) of the disclosure is based on any of the embodiments (25) through (30), wherein the glass-based sample has a side having a side portion, and wherein the moving of the glass-based sample comprises: operably engaging at least one of the side and the side portion with an engagement fixture; and moving the engagement fixture.

A thirty-second embodiment (32) of the disclosure is based on any of the embodiments (25) through (31), wherein moving the glass-based sample comprises: operably supporting the glass-based sample in a frame; operably engaging the frame with an engagement fixture; and moving the engagement fixture.

A thirty-third embodiment (33) of the disclosure is based on any of the embodiments (25) through (32), wherein the scattered light comprises a noise from a non-stress-related scattering feature of the body and a retardation signal from a stress-related scattering feature of the body, and wherein said averaging to form the averaged light distribution reduces a noise contribution to the optical retardance from the noise as compared to using a single measurement of the intensity distribution to calculate the optical retardance.

A thirty-fourth embodiment (34) of the disclosure is based on any of the embodiments (25) through (33), wherein the stress-related scattering feature varies substantially only in a depth direction into the body of the glass-related sample.

A thirty-fifth embodiment (35) of the disclosure is based on any of the embodiments (25) through (34), wherein the glass-based sample has a thickness TH in the range $0.05$ mm $\leq$ TH $\leq 2$ mm.

A thirty-sixth embodiment (36) of the disclosure is based on any of the embodiments (25) through (35), wherein the glass-based sample has a thickness TH in the range $0.2$ mm $\leq$ TH $\leq 2$ mm.

A thirty-seventh embodiment (37) of the disclosure is based on any of the embodiments (25) through (36), wherein the glass-based sample has a thickness TH in the range $0.25$ mm $\leq$ TH $\leq 2$ mm.

A thirty-eight embodiment (38) of the disclosure is based on any of the embodiments (25) through (37), wherein the glass-based sample has a thickness TH in the range $0.3$ mm $\leq$ TH $\leq 2$ mm.

A thirty-ninth embodiment (39) of the disclosure is based on any of the embodiments (25) through (38), wherein the glass-based sample has a thickness TH in the range $0.3$ mm $\leq$ TH $\leq 1$ mm.

Additional features and advantages are set forth in the Detailed Description that follows, and in part will be apparent to those skilled in the art from the description or recognized by practicing the embodiments as described in the written description and claims hereof, as well as the appended drawings. It is to be understood that both the foregoing general description and the following Detailed Description are merely exemplary, and are intended to provide an overview or framework to understand the nature and character of the claims.

BRIEF DESCRIPTION OF THE DRAWINGS

The accompanying drawings are included to provide a further understanding, and are incorporated in and constitute a part of this specification. The drawings illustrate one or more embodiment(s), and together with the Detailed Description explain principles and operation of the various embodiments. As such, the disclosure will become more fully understood from the following Detailed Description, taken in conjunction with the accompanying Figures, in which.

DETAILED DESCRIPTION

Figure 1A:
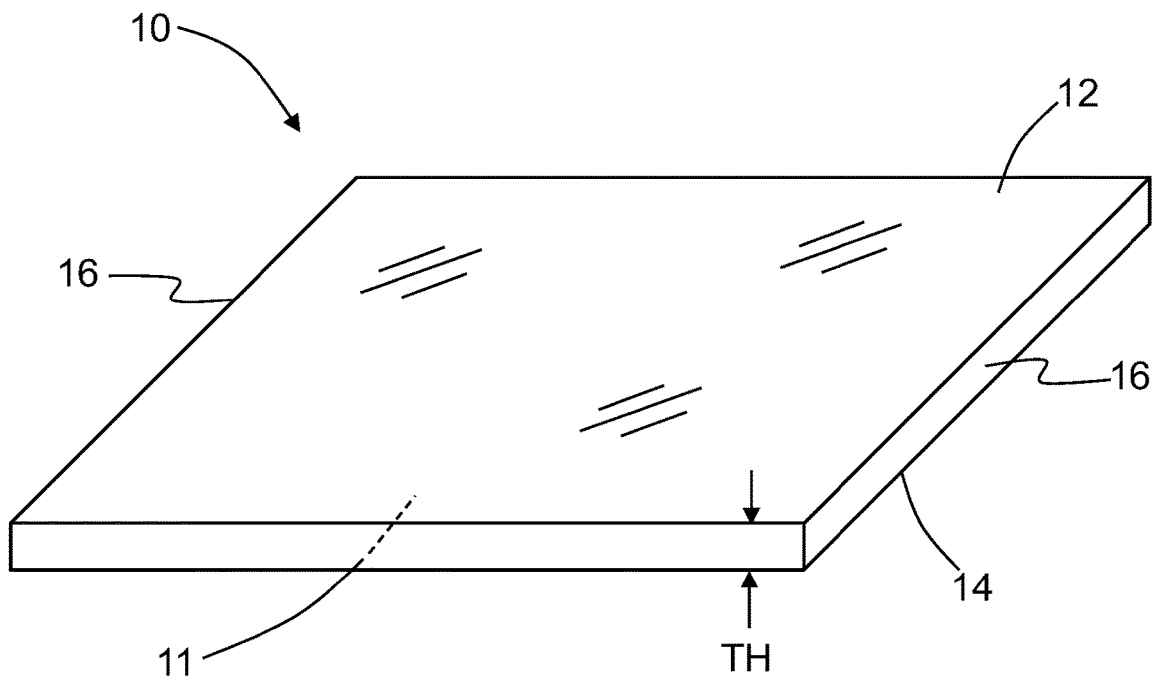
FIG. 1A is an elevated view of an example glass-based sample in the form of a planar sheet.

Reference is now made in detail to various embodiments of the disclosure, examples of which are illustrated in the accompanying drawings. Whenever possible, the same or like reference numbers and symbols are used throughout the drawings to refer to the same or like parts. The drawings are not necessarily to scale, and one skilled in the art will recognize where the drawings have been simplified to illustrate the key aspects of the disclosure.

The claims as set forth below are incorporated into and constitute part of this Detailed Description.

Cartesian coordinates are shown in some of the Figures for the sake of reference and are not intended to be limiting as to direction or orientation.

The term "strengthened" for the glass-based samples considered herein means that the original samples have undergone a process to create some stress profiles that could have a variety of shapes, typically intended to make the samples stronger and thus harder to break. Example strengthening processes include ion exchange, tempering, annealing and like thermal processes.

The abbreviation "ms" stands for "millisecond."

The abbreviation "nm" stands for "nanometer."

The term "glass-based sample" as used herein includes any object made wholly or partly of glass, such as laminates of glass and non-glass materials, laminates of glass and crystalline materials, and glass-ceramics (including an amorphous phase and a crystalline phase). Thus, in an example, the glass-based sample can consist entirely of a glass material while in another example can consist entirely of a glass-ceramic material.

The glass-based samples considered herein generate during a polarimetry measurement a relatively high amount of light scattering by non-stress-based mechanisms within a sample, such by scattering centers, micro-particles, inhomogeneities, crystal structure, Mie or non-selective scattering, multiple scattering, etc. Such light scattering represents noise that is not stress based and can obfuscate the stress characterization. These features generate a noise in the retardation signal in the scattered light, wherein the noise does not include stress-related information that can be used to infer a stress-based characteristic of the sample.

The terms "image" and "line image" are used herein to describe a distribution of light (i.e., intensity distribution) as formed by scattered light at an image sensor of an image sensing device and do not necessarily require an imaging system to define the light distribution.

In the discussion below, the polarimeter is configured to cycle between two or more polarization states (or just "polarizations" for short). In an example, there can be eight or more different polarization states per cycle that combine the linear, elliptical and circular polarizations as is known in the art.

In an example, the "characterizing" of the glass-based samples considered herein includes determining an optical retardance that can be used to calculate one or more stress-based properties of the glass-based sample. In another example, the characterizing of the glass-based sample includes determining one or more stress-based properties of the glass-based sample, such as a stress profile, a surface stress, a depth of compression, a center tension, and a birefringence profile.

In an example below, the minimum sample speed SS is expressed as $SS=K \cdot \lambda/t_E$, where K is called the wavelength smoothing factor, $\lambda$ is the wavelength of light and $t_E$ is the exposure time. This expression for the sample speed SS can be used to determine the sample speed SS to achieve a given distance of movement in terms of the wavelength $\lambda$ for a given exposure time. In an example, $SS \geq K \cdot \lambda/t_E$. In an example, K can in the range from 0.4 to 1, while in another example K can range from 0.5 to 1, while in another example K can range from 0.6 to 1.

Glass-Based Samples

FIG. 1A is an elevated view of an example type of glass-based sample 10 in the form of a planar sheet. The glass-based sample ("sample") 10 has a body 11, a top surface 12, a bottom surface 14 and sides 16. The sample 10 has a thickness TH. In some cases, the sample thickness can be in the range from 0.025 mm≤TH≤2 mm, such as 0.025 mm≤TH≤2 mm, 0.20 mm≤TH≤2 mm, 0.25 mm≤TH≤2 mm, 0.3 mm≤TH≤2 mm, or 0.3 mm≤TH≤1 mm, and any and all sub-ranges formed between these endpoints. The thicknesses TH of the glass-based samples that can be measured using the methods disclosed herein is not limited by polarimeter (discussed below) but rather by the fabrication technology used to make the samples.

Example types of samples 10 can be strengthened (e.g., chemically or thermally strengthened) and comprise either a glass, a ceramic or a glass ceramic. Example types of samples 10 include protective covers for displays and/or housings for mobile devices such as smart phones, tablets, laptop computers, GPS devices, etc. Such samples tend to be thin and planar, such as shown in FIG. 1A.

Figure 1B:
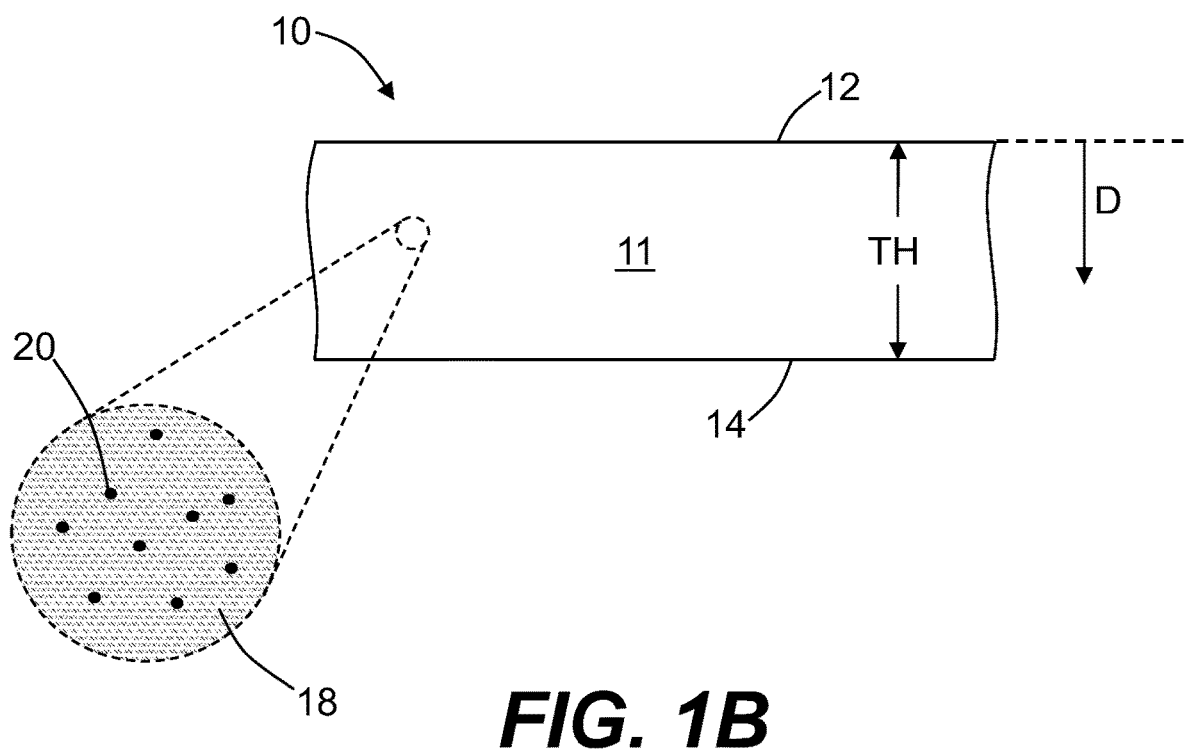
FIG. 1B is a close-up view of the body of the glass-based sample, illustrating the presence of stress-based and non-stress-based scattering features, with the latter giving rise to non-stress-based scattered light that can obfuscate the "retardation signal" defined by stress-based scattered light.

FIG. 1B is a close-up view of a portion of the sample 10 and shows a close-up inset of the body 11 of the sample. The body 11 includes a stress-related (SR) scattering feature 18 that scatters the input light beam while affecting the optical retardation. The body 11 also includes a non-stress-related (NSR) scattering feature 20 that scatters the input light beam by means affecting the optical retardation other than stress within the body 11, as described in greater detail below. The NSR scattering feature 20 can include one or more of scattering centers, particles (e.g., microparticles, nanoparticles, etc.), non-stress related inhomogenieties, crystalline structure, etc. It is assumed that the NSR scattering feature 20 does not have the spatial regularity of the SR scattering feature 18 so that degree of light scattering from the NSR scattering feature differs from place to place within the body 11 of the glass-based sample. In an example, the SR scattering feature 18 is assumed to have a profile that varies substantially only in the depth (D) direction into the body 11 but that is substantially constant in the lateral directions. Thus, light scattering from the SR scattering feature 18 varies with the depth D but not in the lateral directions, whereas the light scattering from the NSR scattering feature 20 varies in the lateral direction as well as in the depth direction. In an example, the variation in light scattering from the NSR scattering feature 20 can be random or quasi-random or have a fixed pattern in a particular measurement.

A property of the given type or types of NSR scattering feature(s) 20 present in the sample 10 is that the resulting scattered light does not include optical retardation information that can be used to determine a stress-related property of the sample, such as a stress profile, center tension (CT), depth of compression (DOC), surface stress, birefringence, etc.

Thus, scattered light from NSR scattering features 20 in a given sample 10 constitutes "noise," whereas scattered light from SR scattering features 18 of the sample constitutes what is referred to herein as the "retardation signal," which is used to determine one or more stress-related characteristics of the sample.

Light-Scattering Polarimetry System

Figure 2A:
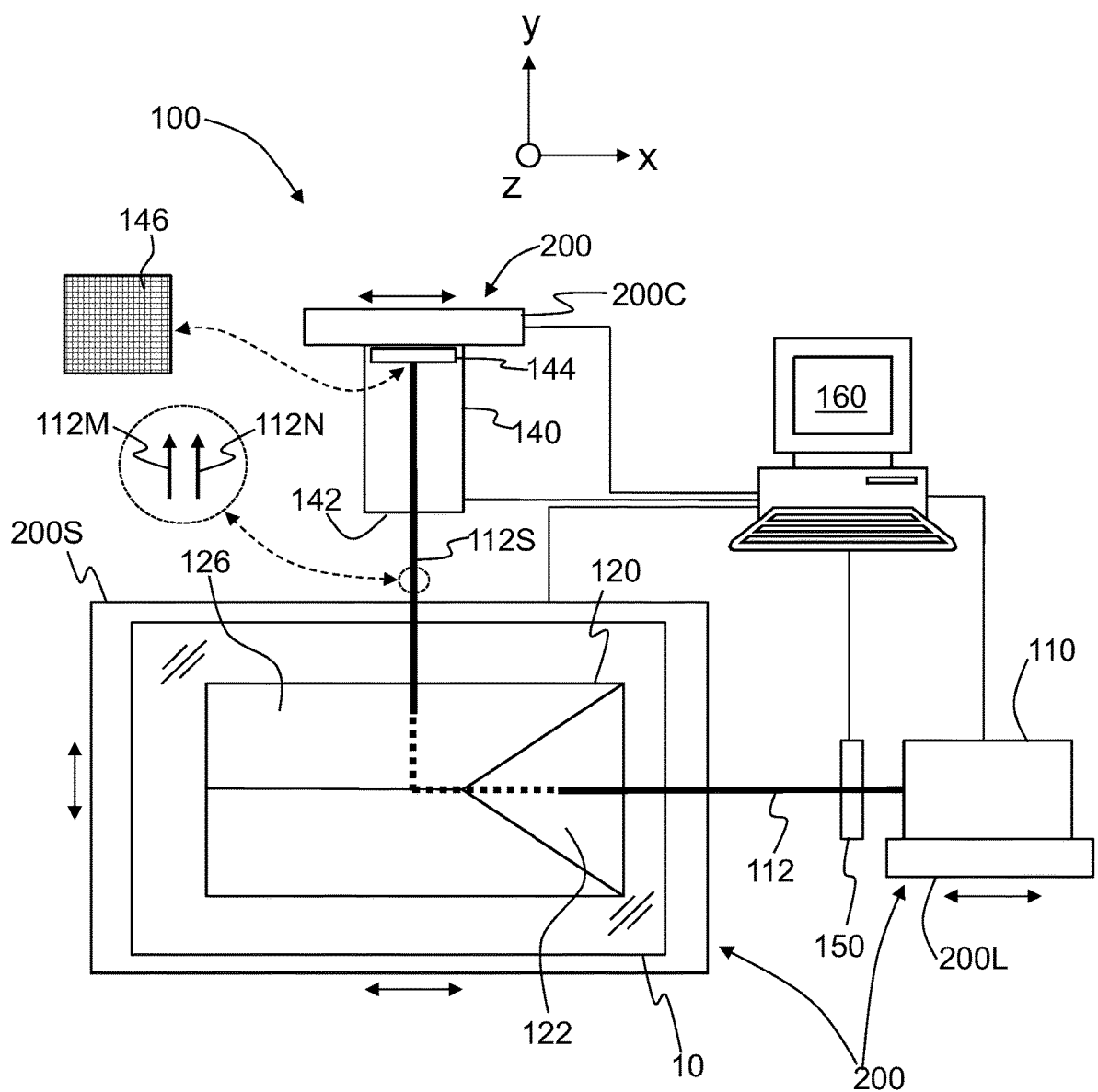
FIGS. 2A, 2B, and 2C are schematic diagrams of an example light scattering polarimetry system ("polarimeter") used to carry out the measurement methods disclosed herein.
Figure 2B:
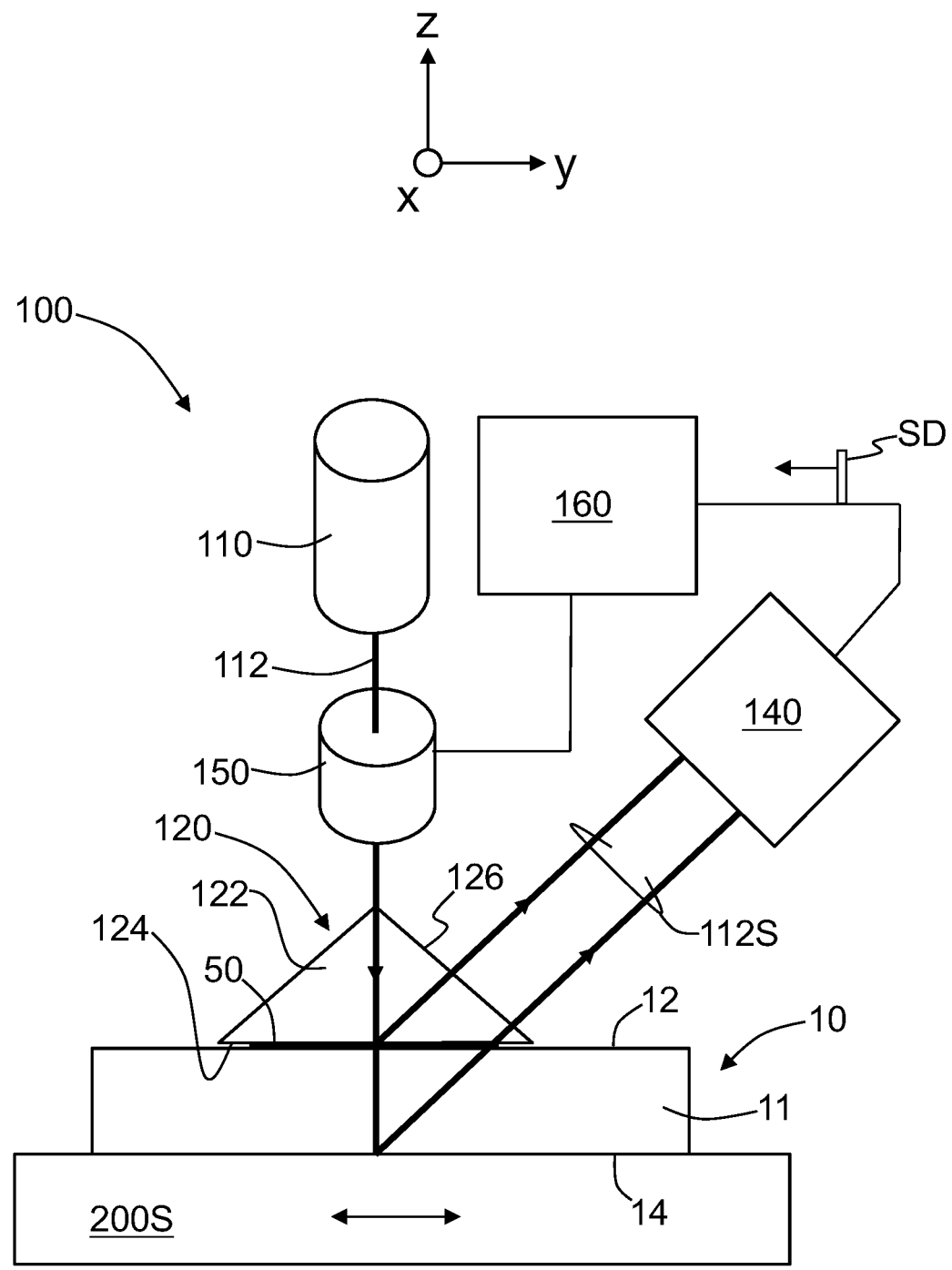

FIGS. 2A and 2B are schematic diagrams of an example light scattering polarimetry system ("polarimeter") 100. The polarimeter 100 includes a laser source 110 that emits a laser light beam 112, which resides in the x-z plane. The light beam 112 has a wavelength λ referred to as the measurement wavelength. The light beam 112 can also be referred to as the input light beam. The light beam 112 is shown as residing in the x-z plane.

The polarimeter 100 includes a prism 120 used to efficiently couple the light beam 112 into the sample 10. The prism 120 includes an input surface 122, a bottom surface 124 and an exit surface 126. In an example, the input light beam 112 is incident upon the input surface 112 at substantially normal incidence thereto to minimize reflections and reduce changes to the input polarization from reflection and refraction. The bottom surface 124 can be interfaced with the top surface 12 of the sample 10 using an index-matching fluid 50 to optimize optical coupling of the input light beam 112 into the body 11 of the sample 10.

The polarimeter 100 also includes an image sensing device 140 having an input end 142. In an example, the image sensing device 140 comprises a digital camera. The image sensing device 140 can comprise an image sensor 144 having an array of imaging pixels 146, which in an example can have a dimension of between 1.8 microns and 10 microns. The image sensing device 140 is disposed adjacent the exit surface 126 of the prism 120.

The polarimeter 100 also includes an optical compensator 150, which is shown disposed in the path of the light beam 112 between the laser source 110 and the prism 120. The optical compensator 150 is configured to continuously change the polarization of the light beam 112 between two or more different polarization states. In an example, the optical compensator 150 is operably connected to a controller 160 that controls the operation of the optical compensator. In an example, the optical compensator 150 can comprise a single liquid crystal device. In another example, the optical compensator 150 can comprise multiple elements such as polarizers, wave plates, filters, prisms (e.g., wedge prisms), etc. The compensator elements (not shown) need not all be disposed in the input light beam 112. In an example, the optical compensator 150 causes the light beam 112 to go through a full polarization cycle (i.e., change between two or more select polarizations) in anywhere from less than 1 second to 10 seconds.

The controller 160 is also operably connected to the image sensing device 140.

With continuing reference to FIGS. 2A and 2B, in an example, the polarimeter 100 includes one or more movement devices 200, namely in one example a first ("laser") movement device 200L configured for moving the laser source 110, a second ("sample") movement device 200S configured for moving the sample 10, and a third ("camera") movement device 200C configured for moving the image sensing device 140. In an example, the movement devices 200 can each comprise a movable stage such a precision stage. Other examples of movement devices 200 are discussed below. The discussion below considers an example polarimeter 100 that has only the second or "sample" movement device 200S for ease of discussion and illustration. Each movement device 200 can be operably connected to and controlled by the controller 160. In an example, the controller 160 is configured with instructions embodied in a non-transitory computer-readable medium to control the operation of polarimeter 100 and perform the calculations for determining at least one stress-related characteristic of the sample 10. The controller 160 can comprise for example a micro-controller, computer, programmable logic controller (PLC), etc.

Figure 2C:
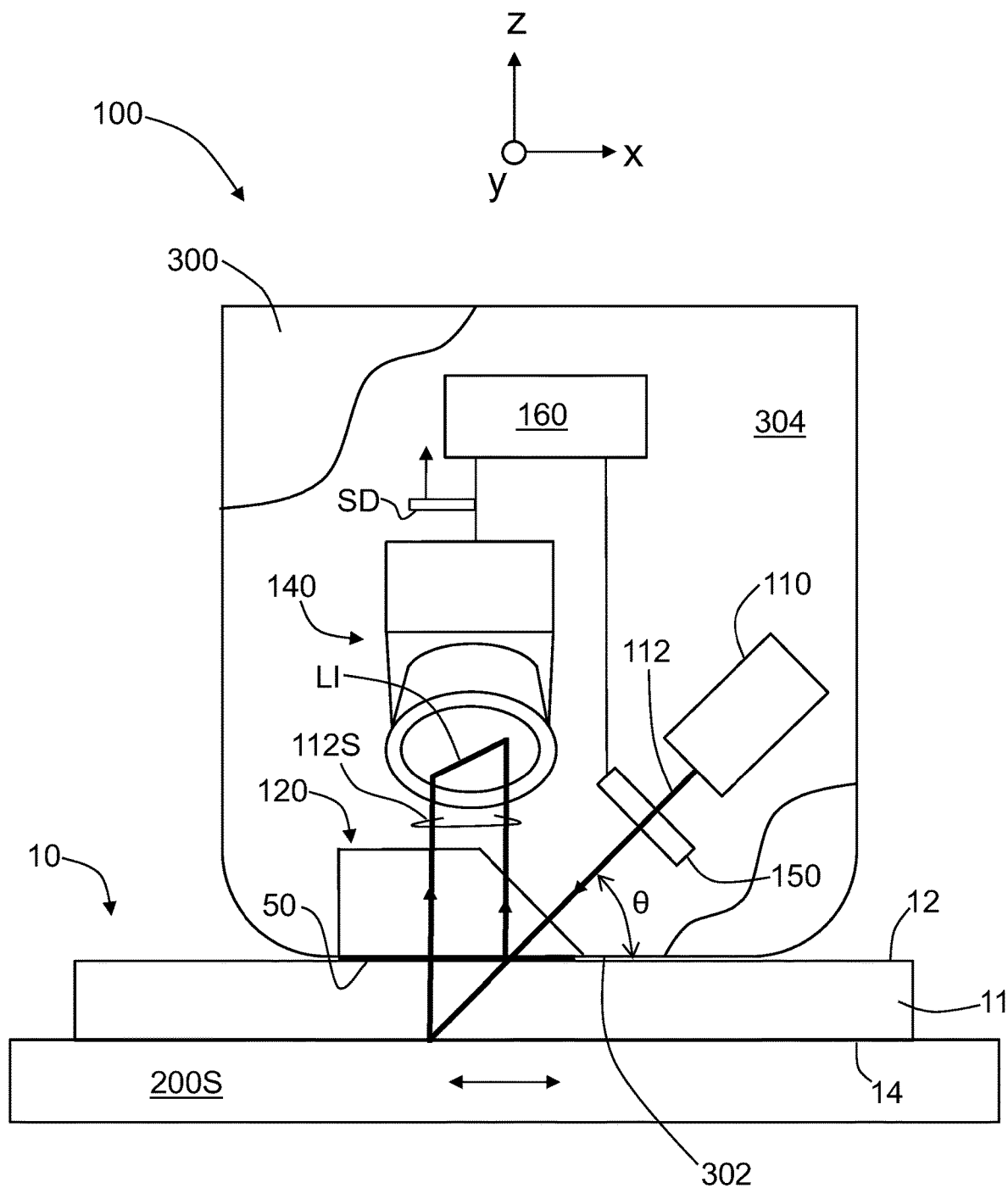
Figure 4A:
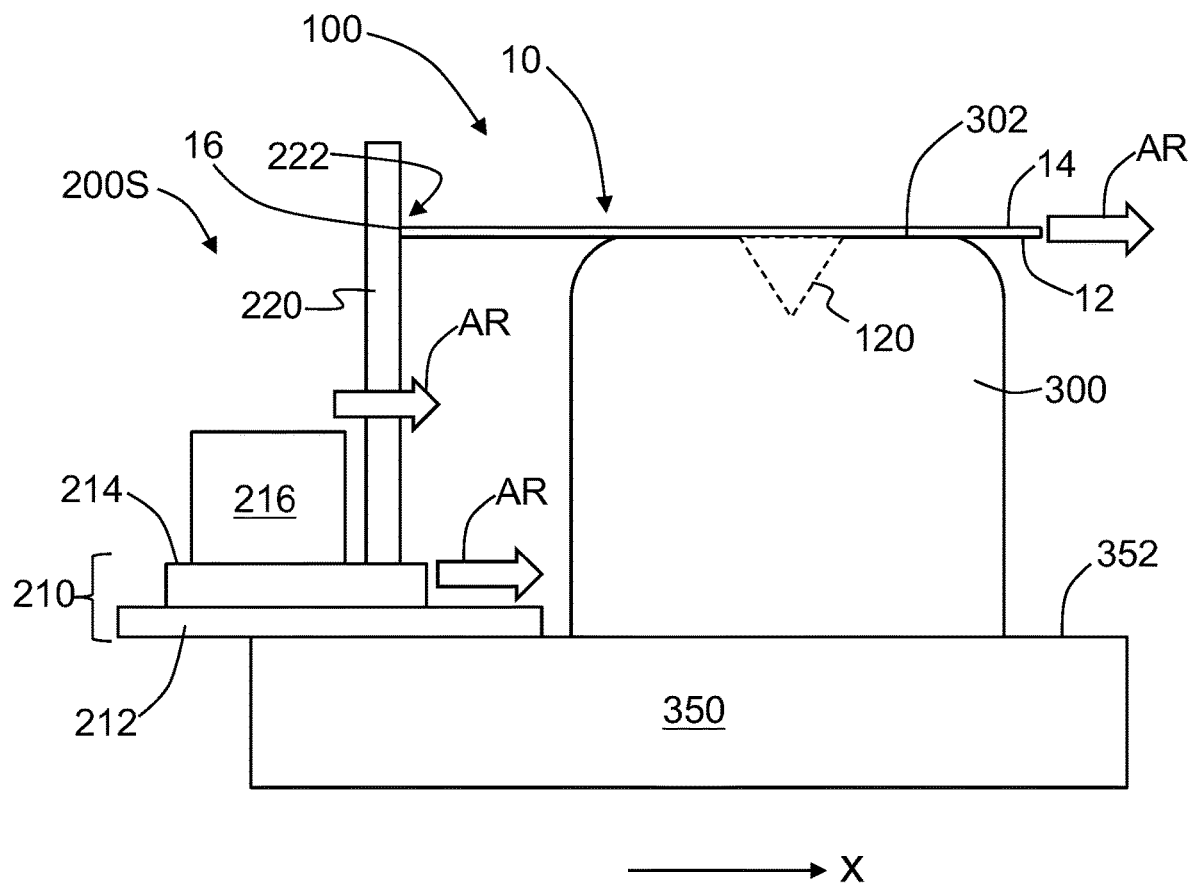
FIGS. 4A and 4B are side views of an example of a polarimeter similar to that shown in FIG. 2C and illustrating example configurations for moving the sample by pushing the sample at one of its sides so that the sample moves along its length in the x-direction (FIG. 4A) or y-direction (FIG. 4B).
Figure 4B:
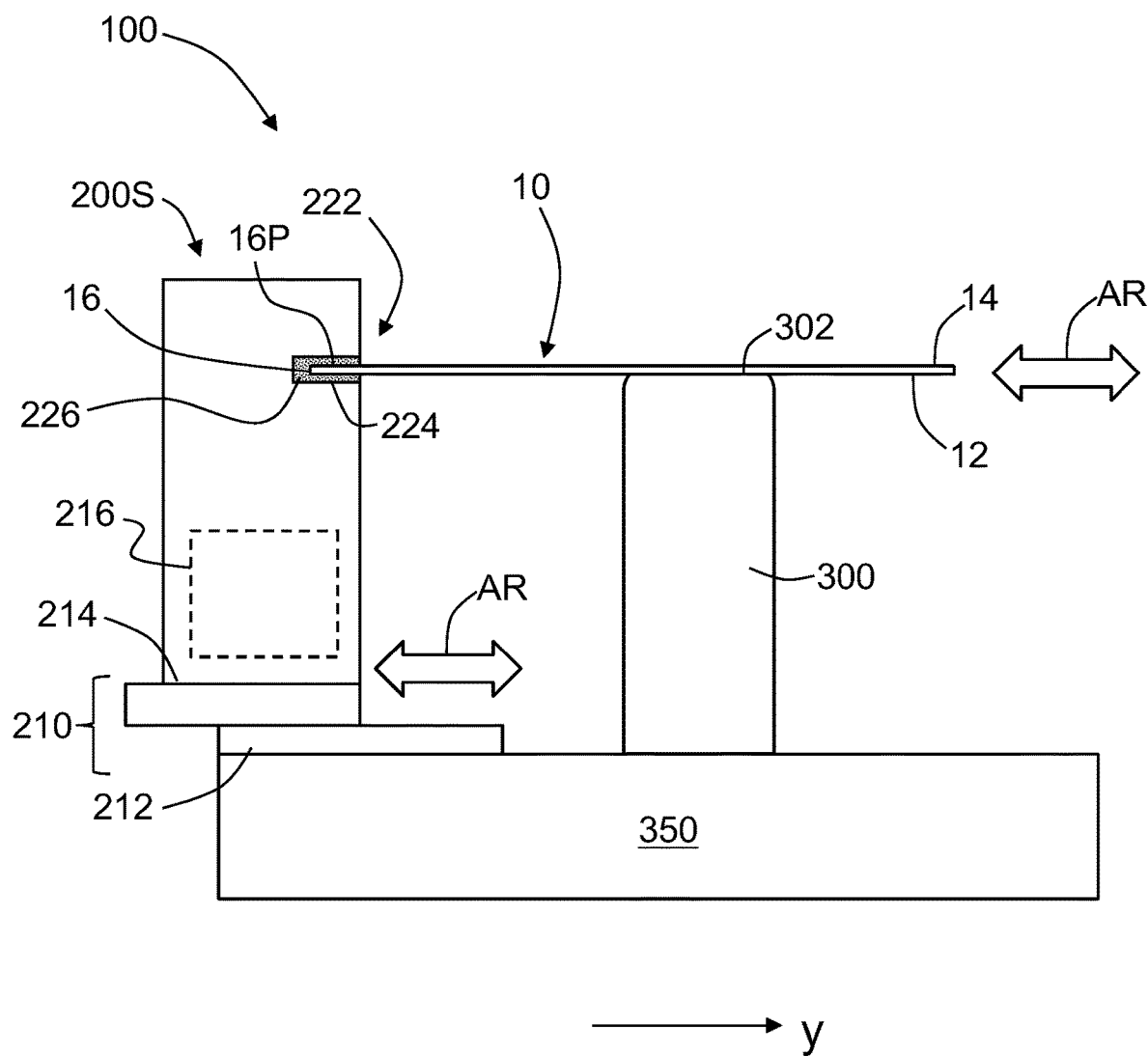

FIG. 2C is a partial cut-away view that shows an example polarimeter 100 that includes a housing 300 having a measurement face 302. The measurement surface 302 can also serve as support surface for the sample 10, as shown in FIGS. 4A and 4B, discussed below. The housing 300 has an interior 304 in which some or all of the aforementioned components of the polarimeter reside. In an example, the housing 300 can be relatively compact, e.g., the size of a typical hand-held device. An example portable polarimeter (polariscope) that has such a housing is the SCALP polariscope (e.g., SCALP-04 or SCALP-05), available from GlassStress Ltd., Talinn, Estonia. In an example, the portable SCALP polariscope can be modified to form the polarimeter 100 and carry out the methods disclosed herein. An example of a larger mechanical configuration for a polarimeter is the SLP series of instruments from Orihara Industrial Co., Ltd., Tokyo, Japan.

With reference now to FIGS. 2A through 2C, in the operation of system 10, the light beam 112 is incident upon the input surface 122 of the prism 120 and travels to the bottom surface 124 of the prism and then through the index-matching fluid 50 and to the top surface 12 of the sample to enter the body 11 of the sample. As noted above, the input light beam 112 has a select polarization at any given time as defined by the optical compensator 150. The (polarized) input light beam 112 is scattered by the body 11 of the sample 10 to form scattered light beam 112S. The scattered light beam 112S exits the sample 10 at the top surface 12, passes back through the index-matching fluid 50 and the bottom surface 124 of the prism 120 and then exits the prism at the output surface 126. The scattered light beam 112S travels to the image sensing device 140 and is captured by the image sensor 144. The scattered light beam 112S forms an image LI on the image sensor 144, as best seen in FIG. 2C and also shown in the close-up view of FIG. 3A.

Figure 3A:
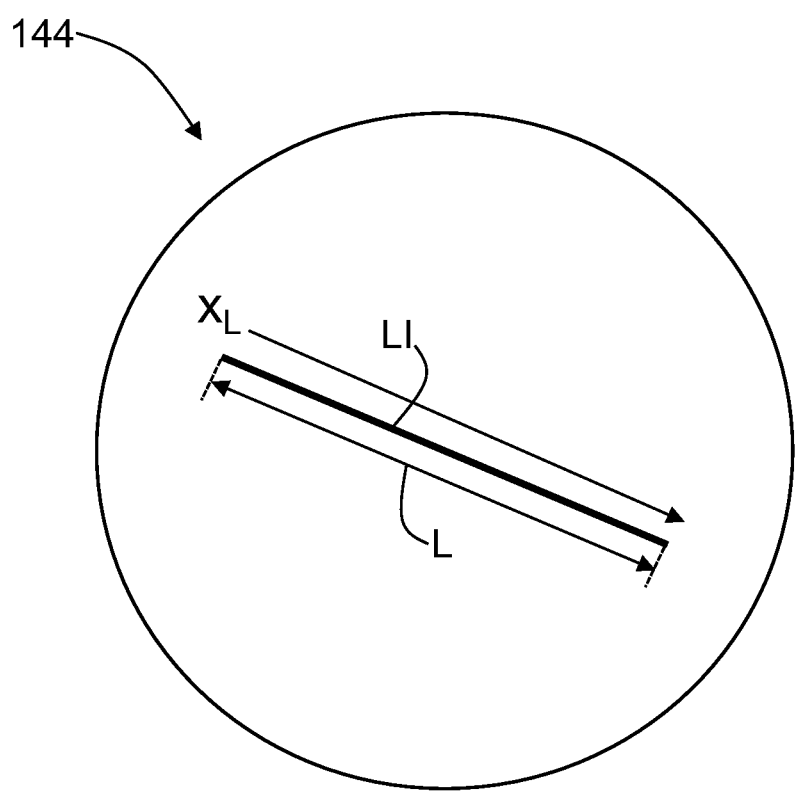
FIG. 3A is a close-up view of the image sensor of the polarimeter of FIG. 2A and showing an example line image formed on the image sensor by light scattered from the sample as part of the measurement process.
Figure 3B:
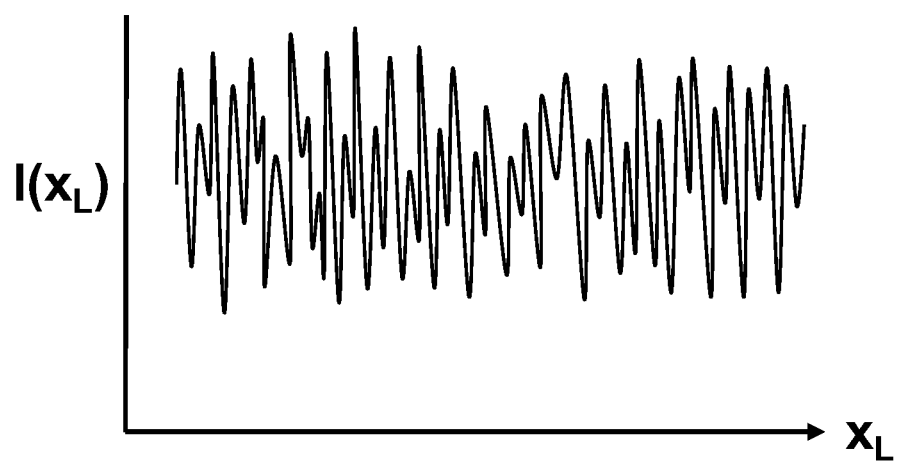
FIG. 3B is a schematic representation of the intensity distribution $I(x_L)$ of the line image formed on the image sensor for a given polarization state of the input light beam.

As shown in FIG. 3A, the image LI is in the form of a line having a length coordinate $x_L$. The line image has an intensity distribution $I(x_L)$ that is measured by the image sensor pixels 146 that coincide with the line image. FIG. 3B is a schematic representation of the intensity distribution $I(x_L)$ of the line image IL formed on the image sensor 144 for a given polarization state of the input light beam 112. The image sensor 144 converts the intensity distribution $I(x_L)$ to an electronic (digital) sensor signal SD, which is sent to the controller 160. In the discussion below, the LI is referred to as a line image since this is the typical type of image shape formed using the polarimeter 100.

In an example, a given measurement of the sample 10 using the polarimeter 100 can involve irradiating the sample with the input light beam 112 for a measurement time $t_M$ of between 1 second and 10 seconds. During the measurement time $t_M$, the polarization state of the light beam 112 varies between the different polarization states, preferably making one or more cycles through the polarization states. Meantime, for each polarization state, the image sensor 144 captures an electronic image of the line image LI during exposure times $t_E$. Prior art polarimeters typically use exposure times $t_E$ that are about the same as the image sensor frame rate FR; for example, an exposure time of $t_E$ of 50 ms, which corresponds to a frame rate FR of 20 frames per second.

The electronically captured line images LI differ in their intensity distribution $I(x_L)$ depending on the polarization state of the input light beam 112 and the optical retardation incurred along the beam path. The difference is due to the difference in the destructive and constructive interference along the length of the scattered light beam 112S as a function of depth D into the sample 10 between the different polarization states. FIG. 3B schematically illustrates just one example of a captured intensity distribution $I(x_L)$ for a given polarization state of the input light beam 112. The differences between the multiple intensity distributions $I(x_L)$ for the different polarization states is used by the controller 160 to calculate the optical retardance OR as a function of depth D into the sample body 11 using relationships well known in the art. Likewise, multiple optical retardance curves OR vs the depth D are calculated using the differences in the intensity distributions $I(x_L)$. For example, for a 3 second measurement time $t_M$ with an image sensor frame rate FR of 20 frames/second, a total of 60 plots of $I(x_L)$ vs. D can be generated to compute OR vs. D and used to calculate one or more stress-related characteristics of the sample 10.

While the intensity distributions $I(x_L)$ necessarily differ between polarization states of the input light beam 112 when there is stress present in the sample 10, the different OR vs. D curves as calculated from the measured intensity distributions should ideally be the same for a given sample at the given measurement location for samples where the stress profile is (ideally) constant.

However, as noted above and as shown in the close-up inset of FIG. 2A, the scattered light beam 112S includes two components, namely a noise component ("noise") 112N formed from the NSR scattering feature 20 within the sample body 11 and a desired measurement component ("retardation signal") 112M formed from the SR scattering feature 18 with the sample body.

Consequently, the measured intensity distribution $I(x_L)$ of the line image LI includes both the noise 112N and the retardation signal 112M so that the variations in intensity in the intensity distribution $I(x_L)$ are not all due to stress alone. Consequently, the different plots of the optical retardation OR versus depth D obtained from the corresponding intensity distributions $I(x_L)$ for the different polarization states will have relatively strong non-stress-related variations that can lead to an imprecise determination of one or more stress characteristics of the sample.

Figure 3C:
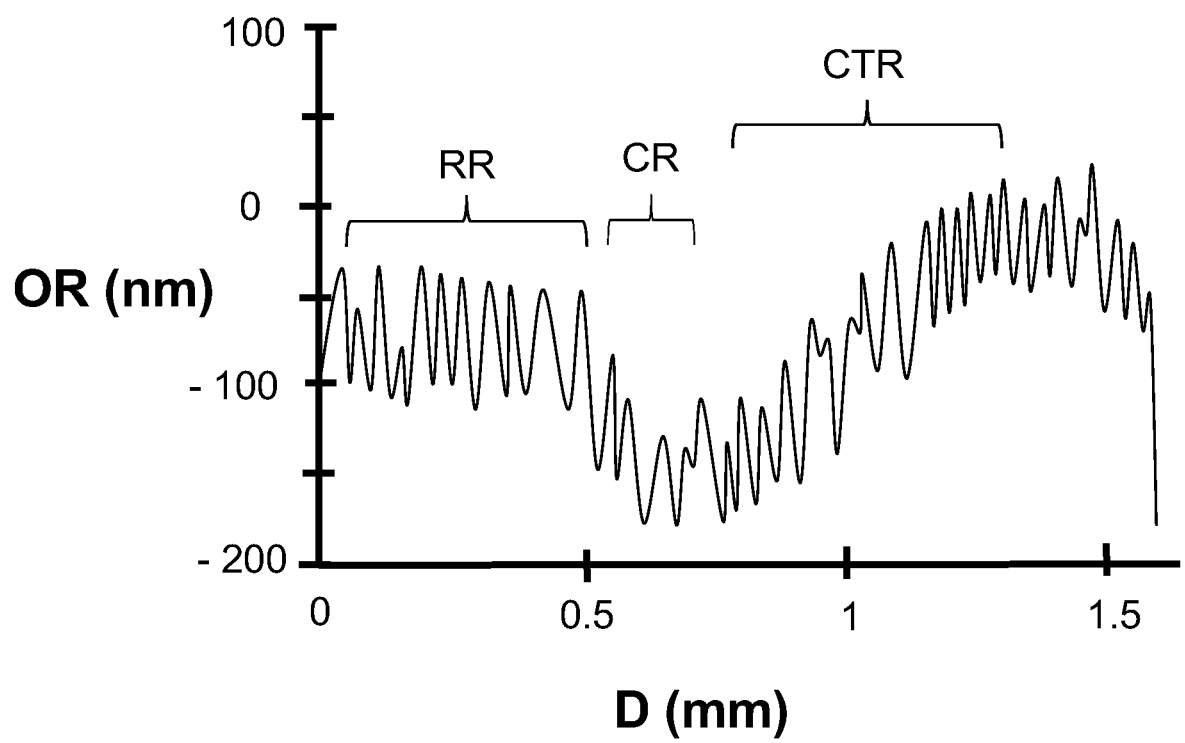
FIG. 3C is a schematic representation of the optical retardation OR (nm) as a function of the distance D (mm) into the body of the sample based on the intensity distributions $I(x_L)$ for the different polarization states.

FIG. 3C is a schematic representation of the optical retardation OR (nm) versus the distance D (mm) into the body 11 of the sample 10 as determined from the measured intensity distributions intensity distributions $I(x_L)$ for the different input polarization states, wherein at least two different polarizations are required and preferably more are used to obtain a better measurement. The exemplary/schematic OR vs. D plot of FIG. 3C is representative of a sample 10 that includes a reference region RR of about 0.5 mm deep that has no stress and thus no slope in the OR data of FIG. 3C. The reference region RR can be formed in one example by the actual sample (i.e., a sample to be measured and characterized) in contact with a reference sample (i.e., a sample having known properties, e.g., by having been previously characterized) as shown in FIG. 4E (introduced and discussed below). In an example, the reference sample is the same as the actual sample but has no internal stress, e.g., by thermally annealing out the stress. The plot of FIG. 3C also shows that the sample 10 being measured also includes a compression region CR from about D=0.5 mm to about 0.75 mm, and then a central tension region CTR from about D=0.75 mm to 1.35 mm and another compression region from about 1.35 to 1.6 mm. Unfortunately, the variations ("noise") in the exemplary OR vs. D plot preclude obtaining a precise value of the stress characteristics of the sample.

To address the problem of measurement noise due to the scattered light 112S including noise 112N, an aspect of the systems and methods disclosed herein include: a) moving the sample 10 relative to one of the light source 110 and the image sensing device 140 when making measurements of the sample 10 so that the intensity distribution $I(x_L)$ obtained for two different portions of the body 11 of the glass sample differ substantially (i.e., varies with time due to glass sample motion); and b) averaging two or more substantially different intensity distributions $I(x_L)$ of the line images LI for a given polarization of the input light beam 112. In examples, the averaging can be performed either by the pixels 146 of the image sensor 144 integrating over the exposure time or by averaging separately detected line images, as explained in greater detail below.

FIG. 4A is a side view of an example of the polarimeter 100 similar to that shown in FIG. 2C. The sample 10 is supported on an upper surface 302 of housing 300 mounted to a stationary support base 350. The stationary support base 350 has an upper surface 352. Also supported by the support base 350 is an example of the sample movement device 200S. The example sample movement device 200S includes a movable stage 210 that has a stage mount 212 and a movable support member 214 that moves relative to the stage mount, which is fixed to the support base 350. The movable stage 210 includes a drive motor 216 that drives the movable support member 214 over the stage mount 212. The movable stage 210 includes an engagement fixture 220 attached to the movable support member 214 and configured to operably engage the sample either directly or indirectly. In one example, the engagement fixture 220 can include a contact or engagement location 222 that contacts or engages a side 16 of the sample 10.

As the movable support member 214 moves in the x-direction, the engagement fixture 220 also moves in the x-direction and pushes the sample 10 in the x-direction and over the measurement face of the housing 300 of the polarimeter 100. Measurement of the sample 10 by polarimeter 100 is carried out as the sample 10 moves relative to the incident light beam 112 from the light source 110. In the example shown in FIGS. 4A and 4B, the light beam 112 resides in a first plane (e.g., the x-z plane, as shown) with the movement of the sample 10 is in second plane (i.e., the x-y plane, as shown). In general, any movement where the laser beam 112 is incident upon different portions of the sample at different times can be utilized.

FIG. 4B is similar to FIG. 4A and shows a configuration wherein the movement of the sample is in the y-direction and wherein the engagement fixture 220 includes a recess 224 at the contact or engagement location 222, with the recess including a resilient material 226 that grips a side portion 16P of the sample 10 without damaging it. This allows for the sample 10 to be moved in a manner that corresponds to movement of the sample movement device 200S. In one example, the movement is back and forth, as indicated by the double-ended movement arrows AR. In another example, the movement can be translational, rotation or a combination thereof (e.g., oscillator, dual action, etc.).

Figure 4C:
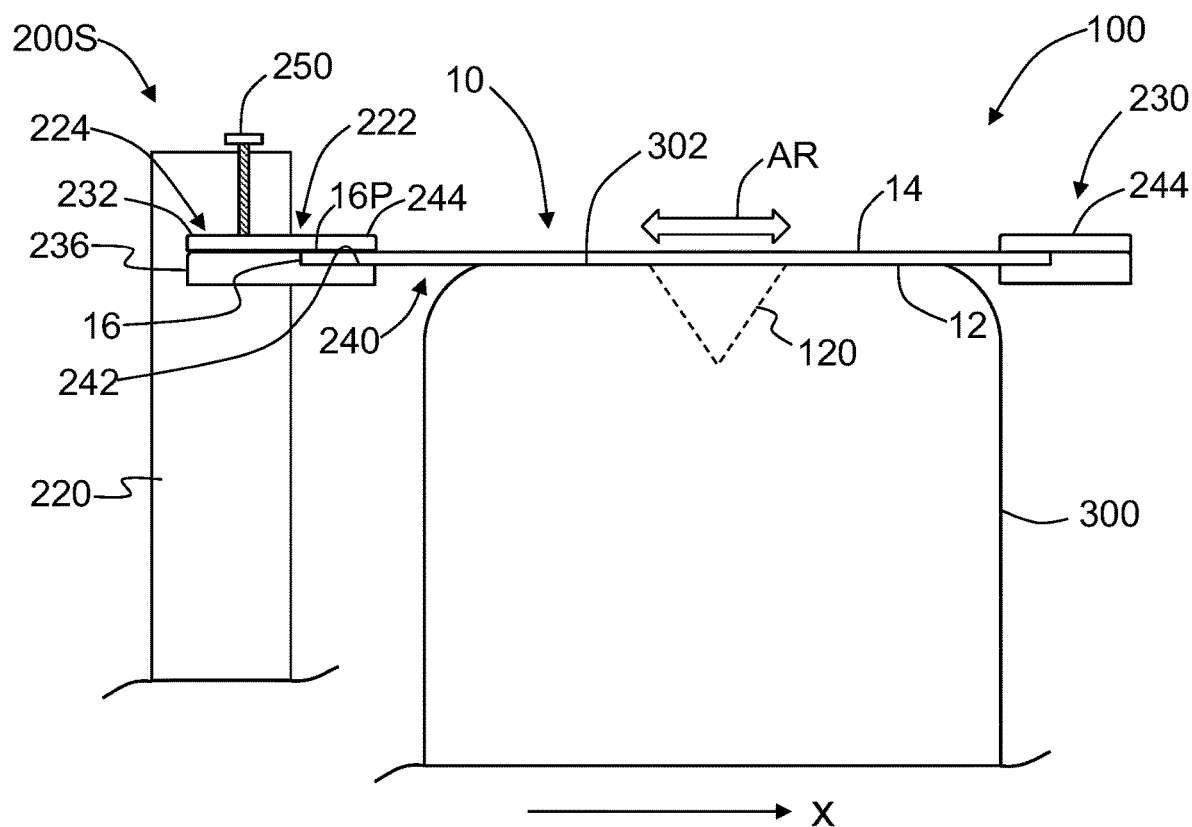
FIG. 4C is similar to FIG. 4A and is a close-up view illustrating an example where the sample is supported by a support frame.
Figure 4D:
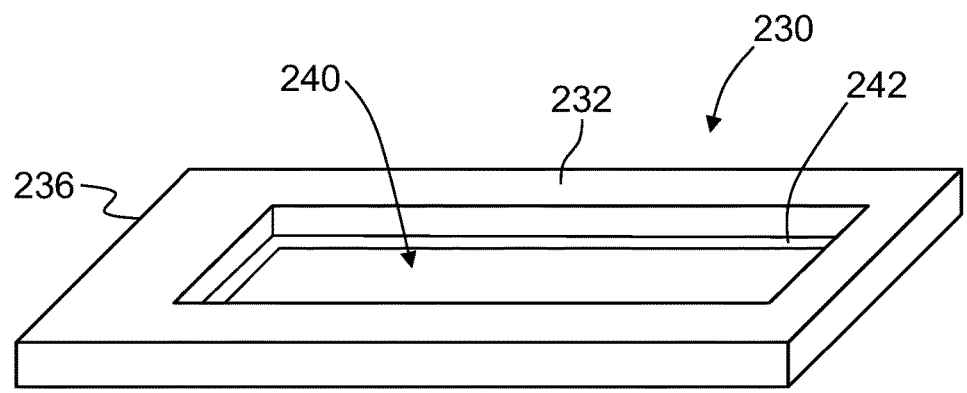
FIG. 4D is an top-down elevated view of an example of the support frame of FIG. 4C.
Figure 4E:
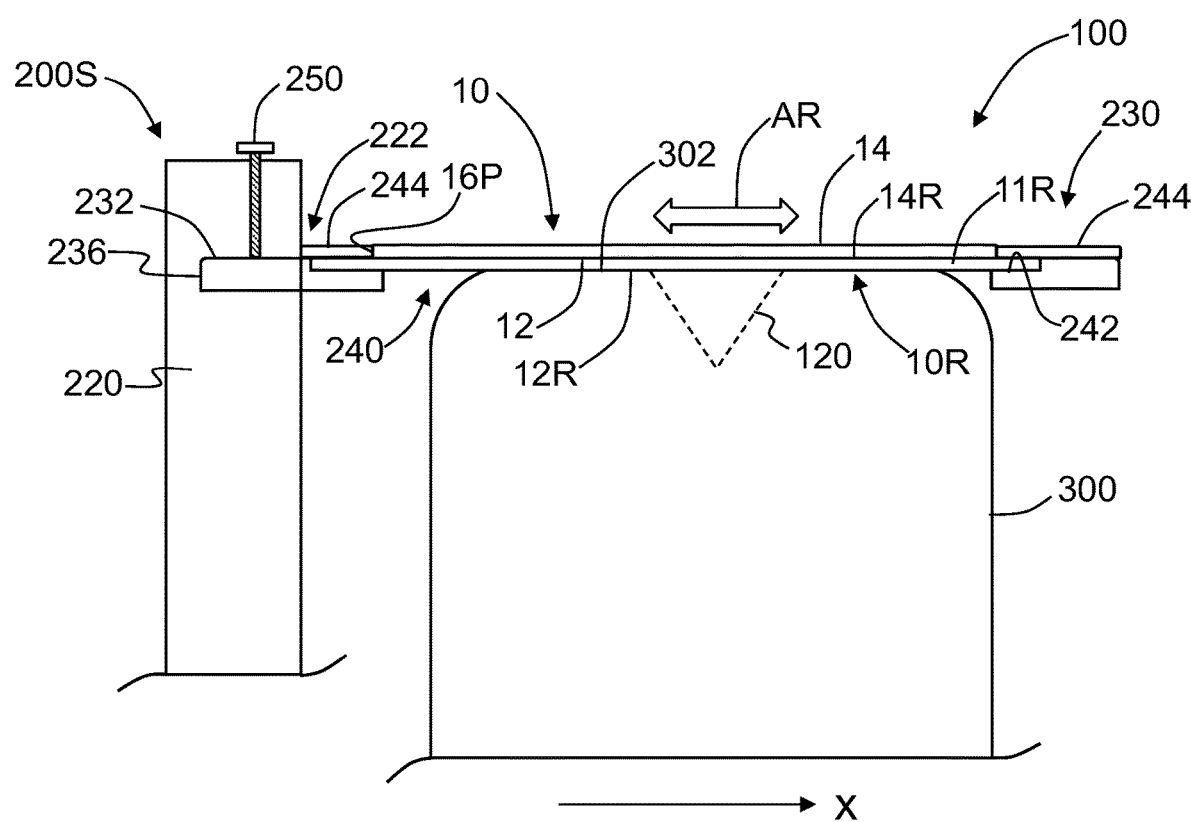
FIG. 4E is similar to FIG. 4C and illustrates an example where a reference sample is supported by the support frame while the sample to be measured resides atop the reference sample.

FIG. 4C is similar to FIG. 4A and is a close-up view illustrating an example where the sample 10 is supported by a support frame 230. FIG. 4D is a top-down elevated view of an example support frame 230. The support frame 230 has a top surface 232, a proximal end 236, and a central opening 240 with an interior ledge 242. The interior ledge 242 is used to support the sample 10 within the support frame 230. A securing member 244 can be placed over a portion of the top surface 232 of the support frame 230 to hold the sample 10 in place within the central opening 240. Other securing means and configurations for holding the sample 10 in the support frame 230 can also be employed. In an example, the support frame 230 can be made of a lightweight and stiff material, such as molded plastic.

The support frame 230 can be held in place in the recess 224 of the engagement fixture 220 using one or more securing members 250, such as one or more set screws. As with the embodiment of FIG. 4B, in one example, the movement of the sample 10 and the support frame 230 is back and forth, as indicated by the double-ended movement arrows AR. In another example, the movement can be translational, rotation or a combination thereof (e.g., oscillator, dual action, etc.).

FIG. 4E is similar to FIG. 4C and illustrates an example wherein a reference sample 10R is supported in the support frame 230. The reference sample 10R has a body 11R, a top surface 12R and a bottom surface 14R. The sample 10 to be measured resides atop the reference sample 10R, i.e., in contact with bottom surface 14R. The reference sample 10R has known (e.g., previously measured) properties. In an example, the reference sample 10R is the same as the sample 10 to be measured, but has been thermally annealed to remove substantially all the stress within the body 11R. This allows for characterizing the light scattering from any non-stress-based scattering features 18 that may be present in the sample 10.

Figure 5A:
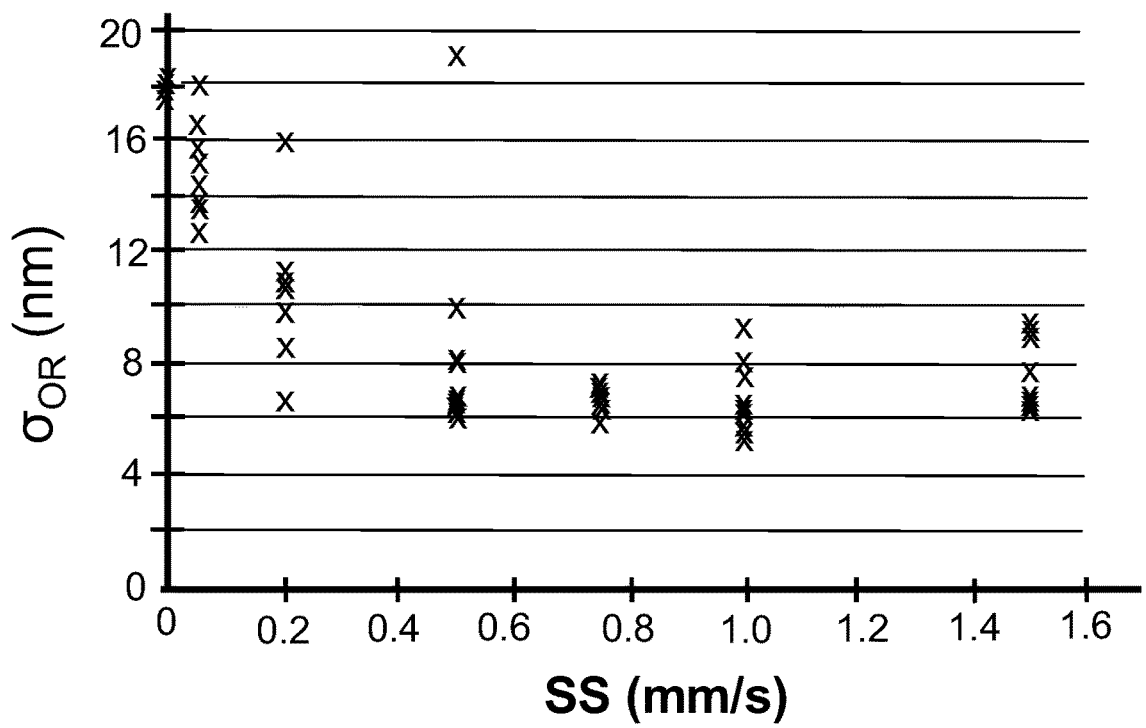
FIGS. 5A and 5B are plots of the standard deviation $\sigma_{OR}$ (nm) of the measured optical retardation OR (nm) versus the sample speed SS (mm/s) for two different directions of motion of the sample at various sample speeds and for movement in the x-direction (FIG. 5A) and in the y-direction, (FIG. 5B).
Figure 5B:
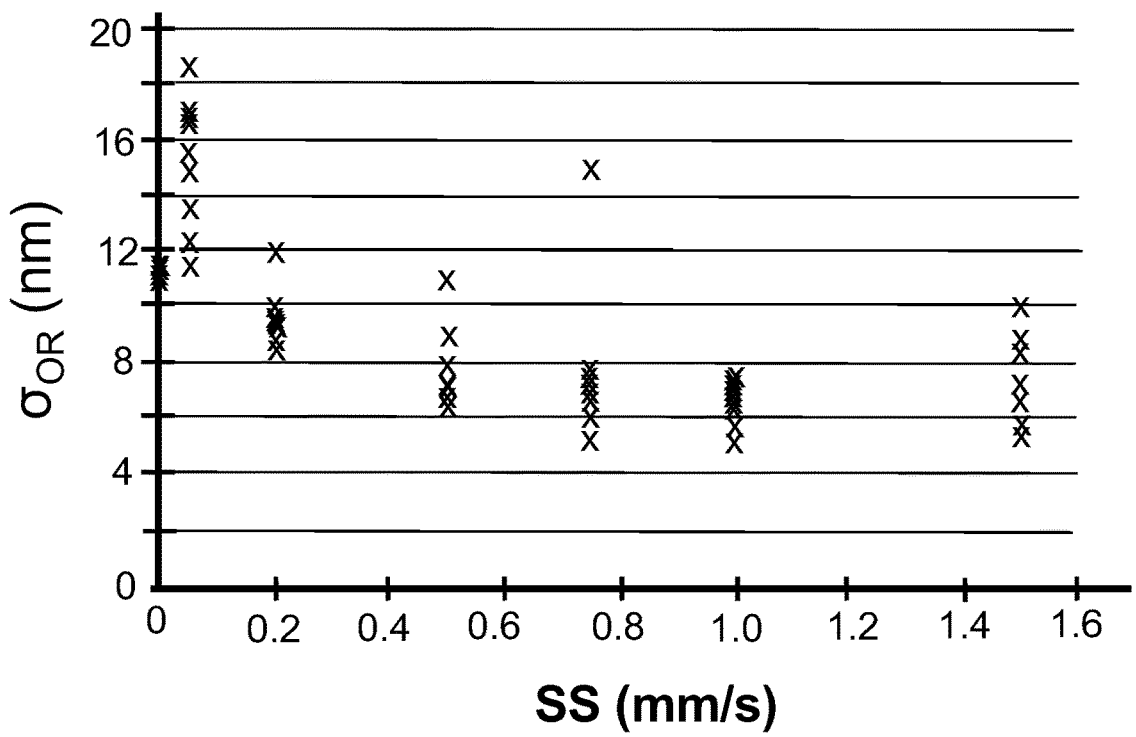

FIGS. 5A and 5B are plots of the standard deviation $\sigma_{OR}$ (nm) of the measured optical retardance OR (nm) versus the sample speed SS (mm/s) as measured by the polarimeter 100 for two different directions of motion of the sample 10, namely in the x-direction, which is at right angles to the image sensing device 140 (FIG. 5A) and in the y-direction, which is at right angles to the incident light beam 112 (FIG. 5B). Multiple (eight) measurements of the optical retardation OR (nm) were taken at each of different speeds SS, namely SS=0 mm/s (i.e., no motion, for reference), 0.05 mm/s, 0.2 mm/s, 0.75 mm/s, 1.00 mm/s and 1.50 mm/s and then the standard deviation $\sigma_{OR}$ of the OR measurements for each speed SS was calculated. This is possible because many measurements of OR vs D can be made over a given measurement time $t_M$ for each of the different polarization states used, as explained in greater detail below. Again, the sample measurement includes a region about 0.5 mm deep that has no stress and thus no slope in the OR data. The plots of FIGS. 5A and 5B indicate that sample speeds SS of about 0.75 mm/s or greater results in substantially reduced measurement noise for the optical retardance OR.

Note that for both plots of $\sigma_{OR}$ (nm) vs. SS (mm/s), for the no-motion data at SS=0 mm/s, the OR standard deviation $\sigma_{OR}$ is substantially constant since the noise from the sample 10 with no motion is substantially constant. With reference again to FIG. 3C, the schematic plot of the optical retardation OR (nm) versus depth D (mm) into the sample in the case of SS=0 mm/s has a relatively large peak-to-peak noise (e.g., peak-to-peak variation or peak-to-peak ratio), which was found to be substantially constant in location and amplitude for each measurement (only one measurement plot is shown in FIG. 3C for ease of illustration).

Figure 6A:
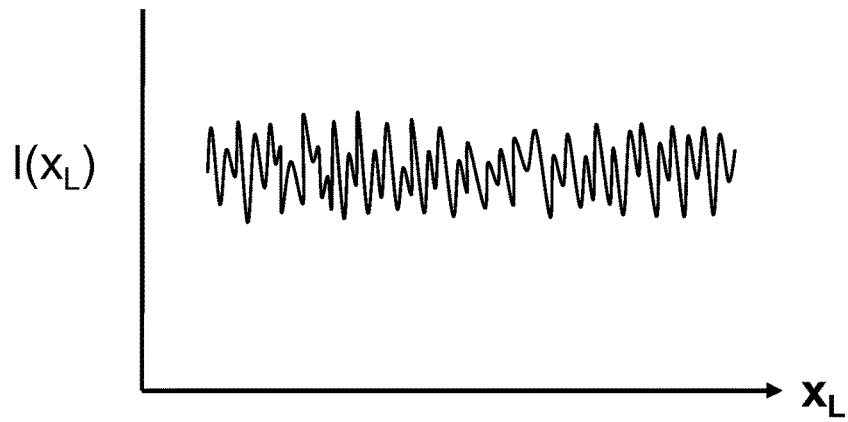
FIG. 6A is similar to FIG. 3B and schematically illustrates the reduction in the variation in the intensity distribution $I(x_L)$ of the line image IL when moving the sample at a speed of about 0.5 mm/s or greater while also averaging the intensity distributions $I(x_L)$ for each polarization state.
Figure 6B:
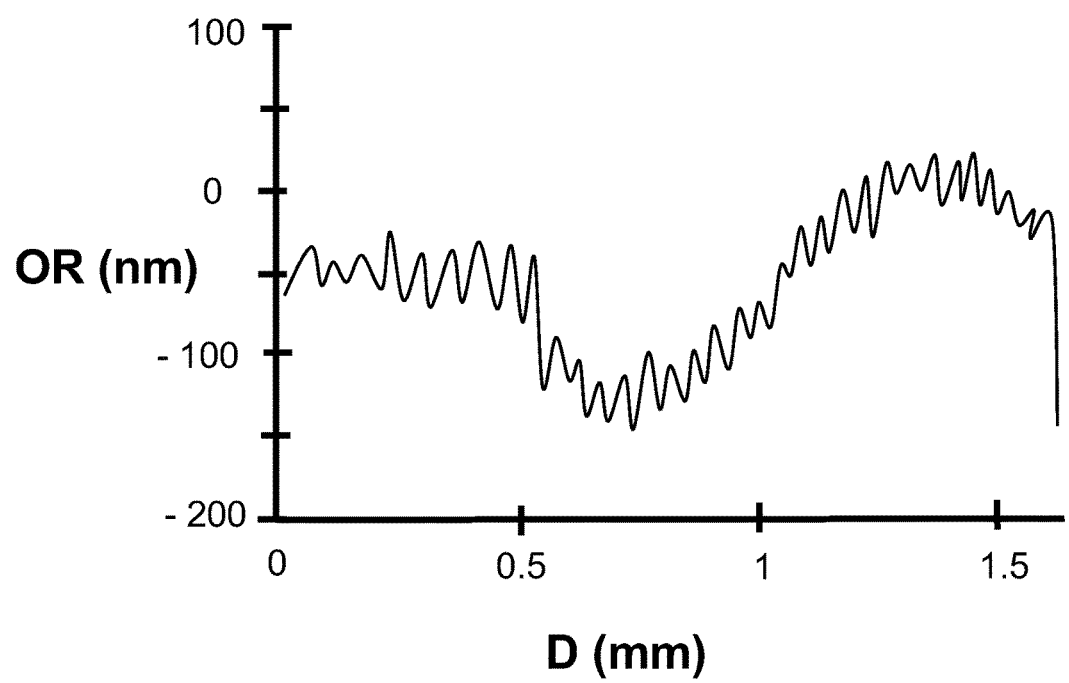
FIG. 6B is similar to FIG. 3C and schematically illustrates the reduction in the variation in the measurement of the optical retardance OR when moving the sample SS and performing the intensity distribution averaging of FIG. 6A.

FIG. 6A is similar to FIG. 3B and schematically illustrates the impact on the intensity distribution $I(x_L)$ of the line image IL when moving the sample 10 at a speed of about 0.5 mm/s or greater, which represents a wavelength smoothing factor K of about 0.4 or greater in the experimental arrangement. FIG. 6B is similar to FIG. 3C and schematically illustrates the impact on the measurement of the optical retardance OR when moving the sample 10 at a speed of about 0.5 mm or greater and performing intensity distribution averaging. The reduction in the peak-to-peak variation in the intensity distribution $I(x_L)$ results in a corresponding reduction in the peak-to-peak variation in the noise of the optical retardance OR, thereby resulting in a more accurate measurement of the stress-related properties of the sample as determined by the measured optical retardance.

Measurement Considerations

The precise sample speed SS and exposure times $t_E$ needed to reduce the measurement noise in the polarimeter 100 to an acceptable level when measuring a sample 10 to characterize at least one stress-related characteristic depends on a number of factors. These factors include the characteristics of the image sensing device 140 (e.g., the gain, image capture rate (frames/second), pixel size, internal pixel average techniques, etc.), as well as the nature of the NSR scattering feature(s) 20, the intensity of the input light beam 112, the number of polarization states used, etc. Other factors include the measurement wavelength $\lambda$ of the light beam 112 from the laser source 110 and the intensity of the scattered light beam 112S. Example measurement wavelengths $\lambda$ can include 640 nm, 518 nm and 405 nm. Example exposure times can range from 0.05 millisecond to 100 milliseconds. Example frame rates FR can range between 10 and 200 frames per second. Example calculations of the optical retardation can utilize between two and two-hundred frames over a measurement time $t_M$ of between 0.1 seconds and 10 seconds.

The line image LI captured by the image sensor 144 has a length L that is the same as the path length of the light beam 112 through the body 11 of the sample based on the configuration of the input end 142 of the image sensor. For an incident angle $\theta$ of the light (measured within the sample and relative to the horizontal; see FIG. 2C), L=TH/sin $\theta$, which for $\theta$=30 degrees gives L=2·TH. For TH=1 mm and pixels 146 having a dimension of between 2 microns and 10 microns, in an example the line image LI is sampled along its length L=2 mm by between about 200 to 1000 pixels.

Averaging the Intensity Distributions

When there is no relative substrate movement (SS=0 mm/s), it has been found that the captured line images IL for a given polarization state have an intensity distribution $I(x_L)$ that is substantially constant (i.e., not time varying) but that has substantial peak-to-valley variations that result in the optical retardance OR vs. D also having large peak to valley variations, with relatively large standard deviations $\sigma_{OR}$ between different OR vs. D curves.

As noted above, aspects of the systems and methods disclosed herein include moving the sample 10 relative to at least one of the light source 110 and the image sensing device 140 while averaging the now time-varying intensity distributions $I(x_L)$ from two or more line images LI. The averaging can be accomplished by integrating within the exposure time of the image sensor 144 for a given measurement polarization associated with different portions of the body 11 of the glass sample. The averaging can also be accomplished by directly averaging the intensity distributions $I(x_L)$ of separately captured (i.e., discrete) line images LI that have not undergone substantial sensor-based averaging.

Averaging the intensity distributions $I(x_L)$ works best when the amount of movement between exposures is sufficient to substantially change the intensity distribution $I(x_L)$ as a function of time while keeping the measurement polarization the same. Without being bound by any particular theory, it is believed from experience and from experimentation on high-scattering samples 10 that the non-stress-based scattering features 20 are not uniformly distributed throughout the body 11 of the sample 10 so that the distribution of such features varies as a function of measurement location. Furthermore, it has been observed that movement distances on the order of the wavelength $\lambda$ of the light beam 112 from the light source 110 can cause a substantial change in the intensity distribution $I(x_L)$ of a line image IL for a given polarization.

For a sample speed SS of 1 mm/s and an exposure time $t_E$ of 1 ms, the sample 10 travels a distance $DS=(SS)(t)=(1 \text{ mm/s})(1\times10^{-3} \text{ s})=1$ micron. This effectively averages the variation in the line image intensity distribution $I(x_L)$ by photon integration in each pixel 146 across the 1 micron of motion distance to define an averaged line image intensity distribution $I_A(x_L)$. The variation in the intensity distribution $I(x_L)$ can also be averaged by first capturing a series of discrete line images and then using the discrete images to compute the average line image intensity distribution $I_A(x_L)$.

For a measurement time $t_M$ of 3 seconds, the total distance traveled $DT=(1 \text{ mm/s})(3 \text{ s})=3$ mm and the total number of exposures captured by the imaging device 140 at 20 frames per second is 60, which is the total number of line images IL captured by the image sensing device 140. The motion between frames is $(1 \text{ mm/s})(\frac{1}{20} \text{ frames per second})=50$ microns. So each frame is associated with a different location of the sample 10.

If the optical compensator 150 is operated in a manner that causes one cycle through the select polarization states in 3 seconds, and there are 60 different polarization states in one cycle, the set of different polarization states is used to calculate the optical retardance OR as a function of depth D into the sample body 11 using relationships well known in the art. In an example, the process is repeated 8 times, each with another 3 seconds of different polarization states. With the motion continuing during the 8 repetitions, each being 3 seconds, the distance traveled between measurements is $(1 \text{ mm/s})(3 \text{ seconds per measurement})=3$ mm.

Figure 7A:
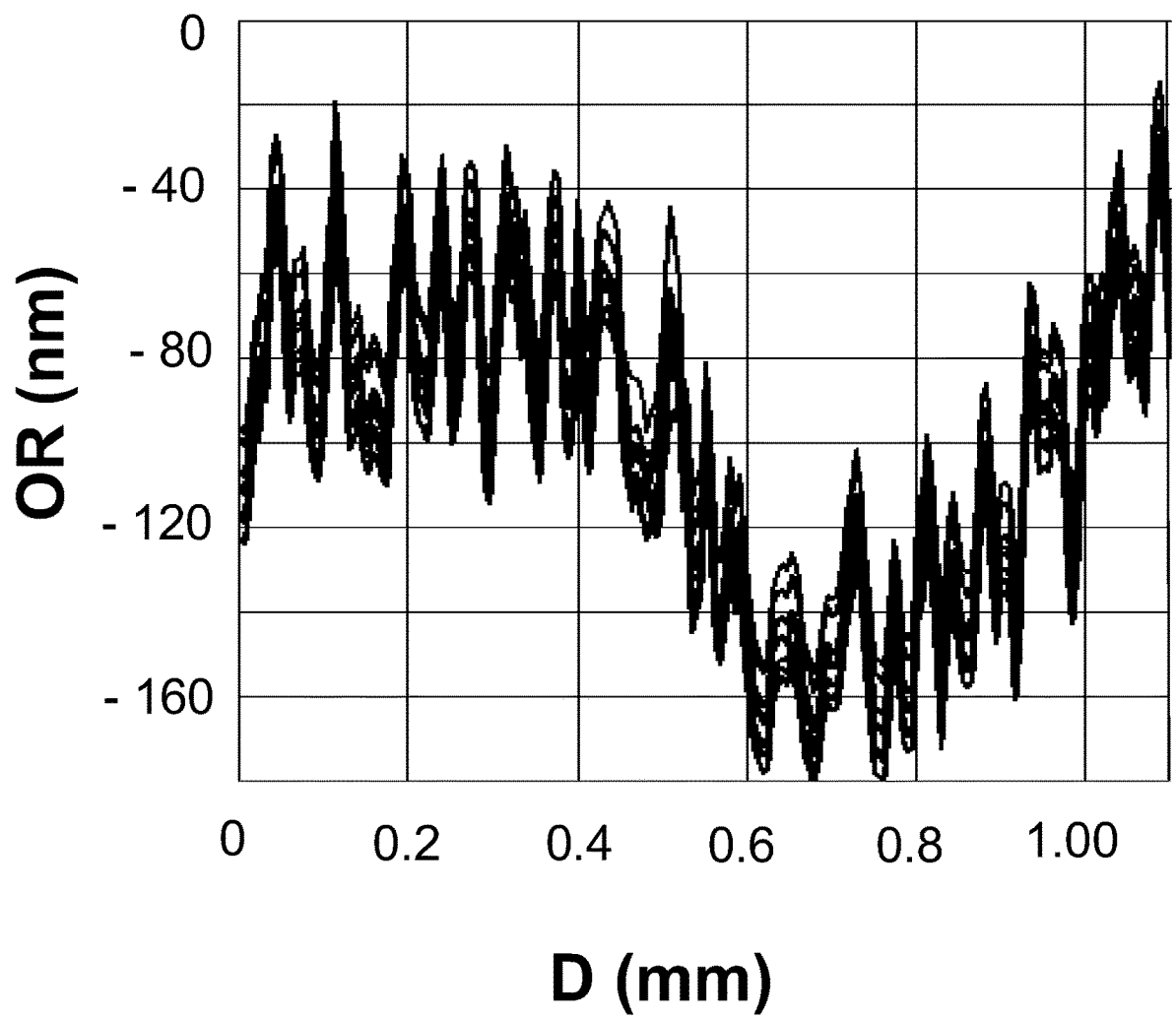
FIG. 7A is a plot of the measured optical retardation OR (nm) vs. D (mm) as measured for a non-moving reference (annealed) and portion (to just past the center) of a strengthened sample, wherein the different curves correspond to different retardation analysis from multiple frames of data as captured by the image sensor over 3 seconds.
Figure 7B:
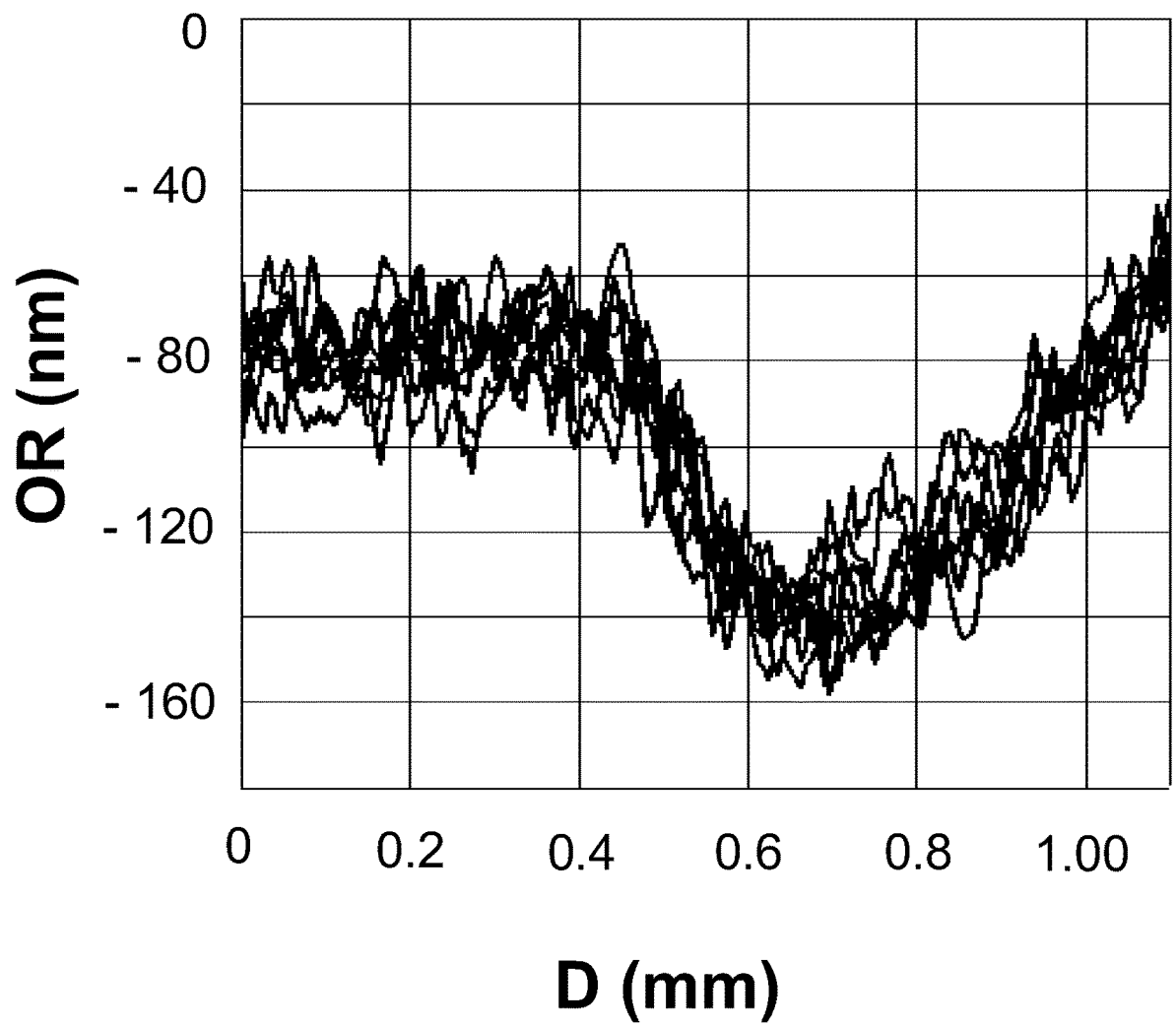
FIG. 7B is similar to FIG. 7A except that the measurement data for the same sample was captured when moving the sample at a sample speed of SS=0.75 mm/s, with the plot showing substantially reduced measurement noise as compared to that of FIG. 7A.
Figure 7C:
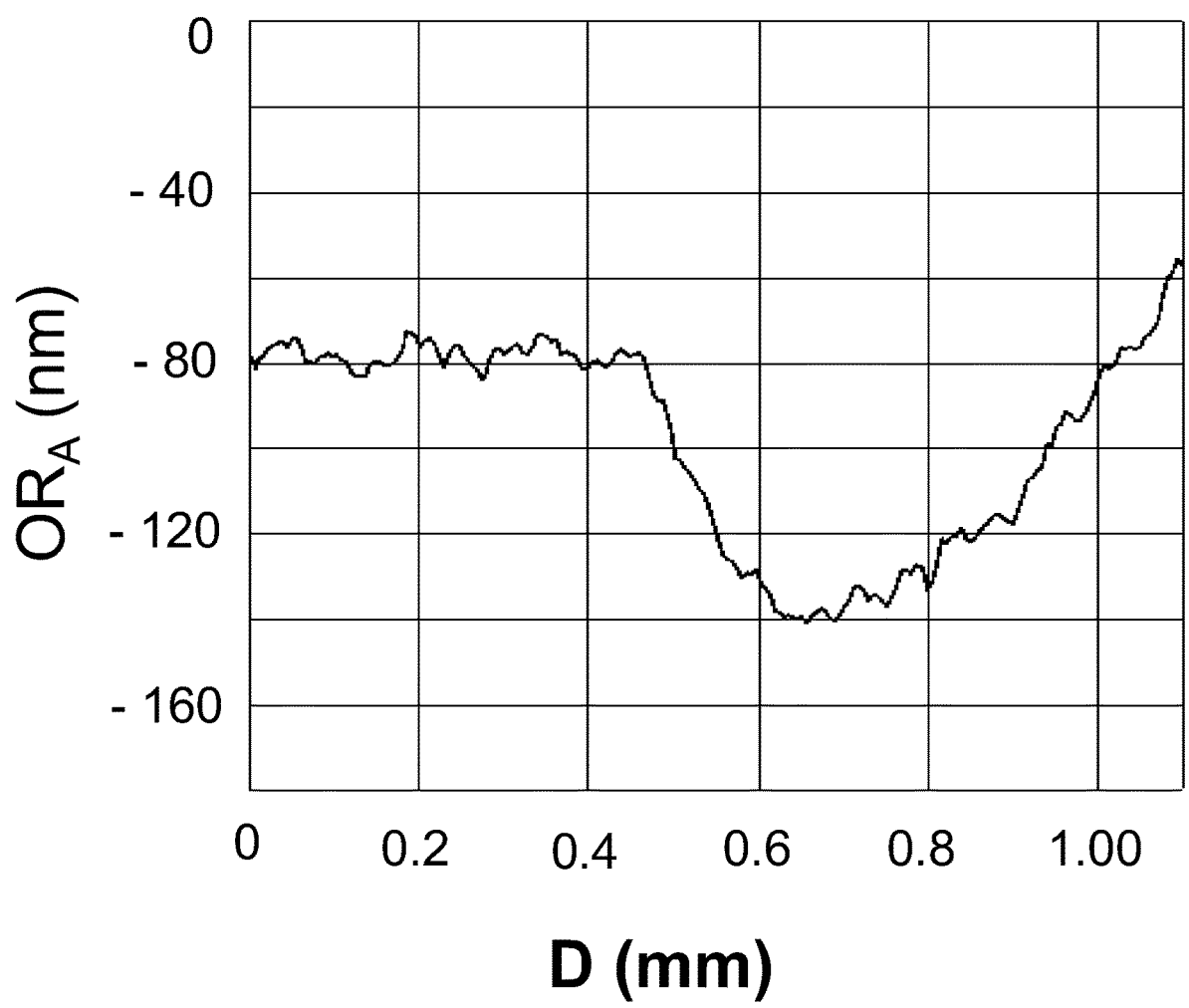
FIG. 7C plots the averaged optical retardation $OR_A$ (nm) vs. D (mm,) wherein the calculations for the optical retardation using the intensity profiles has been done for 4 to 50 sets of frames and the optical retardation results averaged to obtain a single and relatively smooth curve.

A section of an example OR vs. D plot for eight polarization states as measured from an example sample 10 with SS=0 mm/s is shown in FIG. 7A, while the same plot for data captured for the same sample with SS=0.75 mm/s is shown in FIG. 7B. Notable in FIG. 7B is the substantial reduction in measurement noise due to the motion of the sample 10. These now randomly distributed lower levels of noise can be combined with averaging to produce a relatively smooth, single OR vs. D curve, as shown in FIG. 7C.

Since the initial data in the form of line image intensity distribution $I(x_L)$ is collected in increments of the exposure times $t_E$, the distance DS moved during the exposure time is what causes the reduction in noise in the calculation of OR vs. D and ultimately in the improved determination of at least one stress-related characteristic from the OR vs. D data. This can be understood by noting that a cycle through the polarization states is equal to an optical phase distance of 1 wavelength $\lambda$ of the light beam 112, with the various polarization states representing respective fractions of a single wavelength $\lambda$. For example, horizontal and vertical polarizations differ by half a phase distance of wavelength $\lambda$ or equivalently, a phase angle $\phi$ of 180 degrees, where $\phi=2\pi(DS)/\lambda$. For a wavelength $\lambda$ of 500 nm, the distance DS of 1 micron is twice the wavelength $\lambda$ and thus represents twice the total phase of $2\pi$ needed to cycle through the polarization states. In an example, the different positions (portions) of the sample 10 at which measurements are taken are spaced apart by a distance of at least half of the measurement wavelength.

In an example, the sample 10 is moved such that the different portions of the sample at which the measurements are made (i.e., where scattered light 112 is captured) are spaced apart by at least one half the wavelength $\lambda$ of the light beam 112, and further in an example is at least 0.6 wavelength $\lambda$ or at least one wavelength $\lambda$.

By averaging a relatively large number of exposures per frame NE, with each exposure corresponding to multiple line image intensity distributions $I(x_L)$, such as NE 10, the total distance DF traveled by the sample 10 for each frame can be very large compared to the wavelength $\lambda$ of the light beam 112. By way of example, for a sample speed SS of 1 mm/s, a number of exposures per frame NE=10 and an exposure time $t_E$ of 2 ms, the distance traveled per frame $DF=(SS)\cdot(NE)\cdot(t_E)=(1 \text{ mm/s})\cdot(10)\cdot(0.002 \text{ s})=0.02$ mm or 20 microns. This is also a relatively small distance as compared to a typical sample size, which for practical purposes is often at least 5 millimeters long and is usually greater than 10 mm long.

It will be apparent to those skilled in the art that various modifications to the preferred embodiments of the disclosure as described herein can be made without departing from the spirit or scope of the disclosure as defined in the appended claims. Thus, the disclosure covers the modifications and variations provided they come within the scope of the appended claims and the equivalents thereto.

What is claimed is:

1. A method of using light-scattering polarimetry to characterize an optical retardance of a glass-based sample, comprising:
   a. directing a light beam from a light source into the glass-based sample while varying a polarization of the light beam between at least first and second polarization states to generate scattered light for each polarization state;
   b. for each of the at least first and second polarization states, capturing the scattered light with an image sensor having an exposure time $t_E$ and that captures frames at a frame rate FR, wherein the scattered light has an intensity distribution at the image sensor;
   c. moving the sample at a sample speed SS relative to at least one of the light beam and the image sensor so that for each of the at least first and second polarization states, the image sensor averages two or more of the intensity distributions per frame to form an averaged intensity distribution; and
   d. using the averaged intensity distribution for each of at least first and second polarization states to characterize the optical retardance.

2. The method according to claim 1, further comprising using the characterized optical retardance of act d) to determine at least one stress-related characteristic of the glass-based sample.

3. The method according to claim 2, wherein the at least one stress-related characteristic is selected from the group of stress-related characteristics comprising: a stress profile, a surface stress, a depth of compression, a center tension, and a birefringence profile.

4. The method according to claim 1, wherein the act c) of moving the glass-based sample at the sample speed SS relative to at least one of the light beam and image sensor comprises moving the glass-based sample while keeping the light beam and image sensor stationary.

5. The method according to claim 1, wherein the act c) comprises moving the glass-based sample at the sample speed $SS \geq K \cdot \lambda/t_E$, where $\lambda$ is a wavelength of the light beam and K is in the range from 0.4 to 1.

6. The method according to claim 1, wherein the light beam resides in an incident plane and further comprising moving the glass-based sample in a direction perpendicular to the incident plane.

7. The method according to claim 1, wherein the act of moving the sample includes a translation, a rotation, or a combination thereof.

8. The method according to claim 1, wherein the act c) of moving the glass-based sample comprises moving one or both of the laser source and the image sensor while keeping the glass-based sample stationary.

9. A method of determining a stress-based characteristic of a glass-based sample using light-scattering polarimetry, comprising:
operably arranging the glass-based sample in or relative to a polarimeter having an image sensing device, a light source that emits a light beam, and an optical compensator that defines at least first and second polarizations of the light beam;
while moving the glass-based sample relative to the at least one of the light source and the image sensing device, directing the light into the glass based sample to generate scattered light that forms at the image sensing device a line image having a time-varying intensity distribution;
for each of the first and second polarizations, detecting with the image sensing device at least two substantially different intensity distributions;
forming an averaged intensity distribution from the at least two substantially different intensity distributions;
calculating an optical retardation using the averaged intensity distributions for the at least first and second polarizations; and
determining the at least one stress-based characteristic from the optical retardation.

10. The method according to claim 9, wherein forming the averaged intensity distribution comprises detecting the at least two substantially different intensity distributions within a frame of an image sensor that has a frame rate FR.

11. The method according to claim 10, wherein each of the at least two substantially different intensity distributions are detected within an exposure time $t_E$ of between 0.05 millisecond and 100 milliseconds and at the frame rate FR of between 10 and 200 frames per second.

12. The method according to claim 9, wherein the calculating of the optical retardation utilizes between two and two-hundred frames over a measurement time $t_M$ of between 0.1 seconds and 10 seconds.

13. The method according to claim 9, wherein moving the glass-based sample is performed at a speed of at least 0.75 millimeters per second.

14. The method according to claim 9, wherein the light beam resides in an incident plane and further comprising moving the glass-based sample in a direction perpendicular to the incident plane.

15. A method of measuring at least one stress-based characteristic of a glass-based sample having a body, comprising:
a. performing a polarimetry measurement of the glass-based sample for at least first and second polarization states of light having a wavelength $\lambda$ and transmitted into the body of the sample to generate scattered light;
b. during act a), detecting for each of the at least first and second polarization states at least first and second light distributions of the scattered light from different portions of the body and averaging the at least first and second light distributions to form an averaged light distribution;
c. using the averaged light distribution for each of the first and second polarization states to calculate an optical retardance as a function of depth into the body of the glass-based sample; and
d. using the calculated optical retardance to determine the at least one stress-based characteristic of the glass-based sample.

16. The method according to claim 15, wherein said averaging is performed by detecting the at least first and second light distributions within a single frame of an image sensor.

17. The method according to claim 15, wherein the at least first and second light distributions are formed by taking respective at least first and second exposures each having an exposure time $t_E$.

18. The method according to claim 15, further comprising during act a), moving the glass-based sample so that the different portions of the body are spaced apart by at least one half the wavelength of the light.

19. The method according to claim 18, wherein the movement of the glass-based sample has a sample speed $SS \geq K \cdot \lambda/t_E$, where $t_E$ is an exposure time for the first and second exposures used to capture the first and second light distributions, and K is in the range from 0.4 to 1.

20. The method according to claim 15, wherein the scattered light comprises a noise from a non-stress-related scattering feature of the body and a retardation signal from a stress-related scattering feature of the body, and wherein said averaging to form the averaged light distribution reduces a noise contribution to the optical retardance from the noise as compared to using a single measurement of the intensity distribution to calculate the optical retardance.

\* \* \* \* \*

UNITED STATES PATENT AND TRADEMARK OFFICE
CERTIFICATE OF CORRECTION

PATENT NO. : 11,035,730 B2
APPLICATION NO. : 16/667183
DATED : June 15, 2021
INVENTOR(S) : William John Furnas It is certified that error appears in the above-identified patent and that said Letters Patent is hereby corrected as shown below:

On the Title Page

On page 2, in Column 2, item (56), Other Publications, Line 16, delete "Scheimpflung" and insert -- Scheimpflug --, therefor.

In the Claims

In Column 17, Line 35, Claim 9, delete "glass based" and insert -- glass-based --, therefor.

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*